United States Patent
Lowry et al.

(10) Patent No.: US 7,302,298 B2
(45) Date of Patent: Nov. 27, 2007

(54) METHODS AND SYSTEMS EMPLOYING INTRACRANIAL ELECTRODES FOR NEUROSTIMULATION AND/OR ELECTROENCEPHALOGRAPHY

(75) Inventors: David Warren Lowry, Holland, MI (US); Bradford Evan Gliner, Sammamish, WA (US); Kent Leyde, Sammamish, WA (US); Ben Clopton, Bremerton, WA (US); Jay Miazga, Seattle, WA (US); Chris Genau, Seattle, WA (US)

(73) Assignee: Northstar Neuroscience, Inc, Seattle, WA (US)

( * ) Notice: Subject to any disclaimer, the term of this patent is extended or adjusted under 35 U.S.C. 154(b) by 431 days.

(21) Appl. No.: 10/418,796

(22) Filed: Apr. 18, 2003

(65) Prior Publication Data

US 2004/0102828 A1   May 27, 2004

Related U.S. Application Data

(60) Provisional application No. 60/429,481, filed on Nov. 27, 2002.

(51) Int. Cl.
*A61N 1/05* (2006.01)
(52) U.S. Cl. .................................... 607/116
(58) Field of Classification Search ............. 607/115, 607/116, 139; 600/377, 378, 383, 386
See application file for complete search history.

(56) References Cited

U.S. PATENT DOCUMENTS

| | | | |
|---|---|---|---|
| 2,716,226 A * | 8/1955 | Jonas | ..................... 439/805 |
| 2,721,316 A | 10/1955 | Shaw | |
| 3,628,193 A | 12/1971 | Collins | |
| 3,650,276 A | 3/1972 | Burghele et al. | |
| 3,918,461 A | 11/1975 | Cooper | |
| 4,030,509 A | 6/1977 | Heilman et al. | |
| 4,125,116 A | 11/1978 | Fischell | |
| 4,140,133 A | 2/1979 | Kastrubin et al. | |

(Continued)

FOREIGN PATENT DOCUMENTS

DE    19750043 A1    5/1999

(Continued)

OTHER PUBLICATIONS

Pirotte, Benoit, M.D., et al., "The Zeiss-MKM system for frameless image-guided approach in epidural motor cortex stimulation for central neuropathic pain," Sep. 2001, pp. 1-6, vol. 11, Article 3.

(Continued)

*Primary Examiner*—Mark Bockelman
*Assistant Examiner*—Eric D. Bertram
(74) *Attorney, Agent, or Firm*—Perkins Coie LLP

(57) ABSTRACT

Aspects of the invention relate to intracranial electrodes and methods for implanting and using intracranial electrodes. In one particular example, an intracranial electrode includes a shaft having a distal contact surface adapted to electrically contact a surface of a patient's brain, a head associated with the shaft, and threads adapted to fix the electrode with respect to the patient's skull. This electrode may have an adjustable length adapted to change a contact force of the distal contact surface against the surface of the brain by adjusting the length of the electrode.

36 Claims, 14 Drawing Sheets

U.S. PATENT DOCUMENTS

| | | |
|---|---|---|
| 4,214,804 A | 7/1980 | Little |
| 4,245,645 A | 1/1981 | Picard et al. |
| 4,308,868 A | 1/1982 | Jhabvala |
| 4,328,813 A * | 5/1982 | Ray .................... 607/139 |
| 4,340,038 A | 7/1982 | McKean |
| 4,431,000 A | 2/1984 | Butler et al. |
| 4,474,186 A | 10/1984 | Ledley et al. |
| 4,487,210 A | 12/1984 | Knudsen et al. |
| 4,542,752 A | 9/1985 | DeHaan et al. |
| 4,590,946 A | 5/1986 | Loeb |
| 4,607,639 A | 8/1986 | Tanagho et al. |
| 4,646,744 A | 3/1987 | Capel |
| 4,702,254 A | 10/1987 | Zabara |
| 4,844,075 A | 7/1989 | Liss et al. |
| 4,865,048 A | 9/1989 | Eckerson |
| 4,936,306 A | 6/1990 | Doty |
| 4,969,468 A | 11/1990 | Byers et al. |
| 5,002,053 A | 3/1991 | Garcia-Rill et al. |
| 5,024,226 A | 6/1991 | Tan |
| 5,031,618 A | 7/1991 | Mullett |
| 5,054,906 A | 10/1991 | Lyons, Jr. |
| 5,063,932 A | 11/1991 | Dahl et al. |
| 5,092,835 A | 3/1992 | Schurig et al. |
| 5,121,754 A | 6/1992 | Mullett |
| 5,143,089 A | 9/1992 | Alt |
| 5,169,384 A | 12/1992 | Bosniak et al. |
| 5,184,620 A | 2/1993 | Cudahy et al. |
| 5,193,540 A | 3/1993 | Schulman et al. |
| 5,215,086 A | 6/1993 | Terry, Jr. et al. |
| 5,215,088 A | 6/1993 | Normann et al. |
| 5,224,491 A | 7/1993 | Mehra |
| 5,255,678 A | 10/1993 | Deslauriers et al. |
| 5,263,967 A | 11/1993 | Lyons, III et al. |
| 5,271,417 A | 12/1993 | Swanson et al. |
| 5,282,468 A | 2/1994 | Klepinski |
| 5,292,252 A | 3/1994 | Nickerson et al. |
| 5,299,569 A | 4/1994 | Wernicke et al. |
| 5,303,705 A | 4/1994 | Nenov |
| 5,304,206 A | 4/1994 | Baker, Jr. et al. |
| 5,314,458 A | 5/1994 | Najafi et al. |
| 5,358,513 A | 10/1994 | Powell, III et al. |
| 5,370,672 A | 12/1994 | Fowler et al. |
| 5,405,375 A | 4/1995 | Ayers et al. |
| 5,406,957 A | 4/1995 | Tansey |
| 5,411,540 A | 5/1995 | Edell et al. |
| 5,417,719 A | 5/1995 | Hull et al. |
| 5,423,864 A | 6/1995 | Ljungstroem |
| 5,464,446 A * | 11/1995 | Dreessen et al. ........... 607/116 |
| 5,520,190 A | 5/1996 | Benedict et al. |
| 5,522,864 A | 6/1996 | Wallace et al. |
| 5,537,512 A | 7/1996 | Hsia et al. |
| 5,540,734 A | 7/1996 | Zabara |
| 5,540,736 A | 7/1996 | Haimovich et al. |
| 5,549,655 A | 8/1996 | Erickson |
| 5,562,708 A | 10/1996 | Combs et al. |
| 5,575,813 A | 11/1996 | Edell et al. |
| 5,591,216 A | 1/1997 | Testerman et al. |
| 5,593,432 A | 1/1997 | Crowther et al. |
| 5,601,611 A | 2/1997 | Fayram et al. |
| 5,611,350 A | 3/1997 | John |
| 5,618,531 A | 4/1997 | Cherksey |
| 5,628,317 A | 5/1997 | Starkebaum et al. |
| 5,674,251 A | 10/1997 | Combs et al. |
| 5,676,655 A | 10/1997 | McCulloch et al. |
| 5,683,422 A | 11/1997 | Rise |
| 5,702,429 A | 12/1997 | King |
| 5,707,334 A | 1/1998 | Young |
| 5,711,316 A | 1/1998 | Elsberry et al. |
| 5,713,922 A | 2/1998 | King |
| 5,713,923 A | 2/1998 | Ward et al. |
| 5,716,377 A | 2/1998 | Rise et al. |
| 5,722,401 A | 3/1998 | Pietroski et al. |
| 5,725,377 A | 3/1998 | Lemler et al. |
| 5,735,814 A | 4/1998 | Elsberry et al. |
| 5,738,521 A | 4/1998 | Dugot |
| 5,750,376 A | 5/1998 | Weiss et al. |
| 5,752,979 A | 5/1998 | Benabid |
| 5,769,778 A | 6/1998 | Abrams et al. |
| 5,772,591 A | 6/1998 | Cram |
| 5,782,798 A | 7/1998 | Rise |
| 5,782,873 A | 7/1998 | Collins |
| 5,792,186 A | 8/1998 | Rise |
| 5,797,970 A | 8/1998 | Pouvreau |
| 5,814,014 A | 9/1998 | Elsberry et al. |
| 5,814,092 A | 9/1998 | King |
| 5,824,021 A | 10/1998 | Rise |
| 5,824,030 A | 10/1998 | Yang et al. |
| 5,832,932 A | 11/1998 | Elsberry et al. |
| 5,833,709 A | 11/1998 | Rise et al. |
| 5,843,148 A | 12/1998 | Gijsbers et al. |
| 5,843,150 A | 12/1998 | Dreessen et al. |
| 5,865,842 A * | 2/1999 | Knuth et al. ................. 607/116 |
| 5,871,517 A | 2/1999 | Abrams et al. |
| 5,885,976 A | 3/1999 | Sandyk |
| 5,886,769 A | 3/1999 | Zolten |
| 5,893,883 A | 4/1999 | Torgerson et al. |
| 5,904,916 A | 5/1999 | Hirsch |
| 5,913,882 A | 6/1999 | King |
| 5,916,171 A | 6/1999 | Mayevsky |
| 5,925,070 A | 7/1999 | King et al. |
| 5,938,688 A | 8/1999 | Schiff |
| 5,938,689 A | 8/1999 | Fischell et al. |
| 5,941,906 A | 8/1999 | Barreras, Sr. et al. |
| 5,964,794 A | 10/1999 | Bolz et al. |
| 5,975,085 A | 11/1999 | Rise |
| 5,978,702 A | 11/1999 | Ward et al. |
| 5,983,140 A | 11/1999 | Smith et al. |
| 6,006,124 A * | 12/1999 | Fischell et al. ............. 600/378 |
| 6,011,996 A | 1/2000 | Gielen et al. |
| 6,016,449 A | 1/2000 | Fischell et al. |
| 6,018,682 A | 1/2000 | Rise |
| 6,021,352 A | 2/2000 | Christopherson et al. |
| 6,026,326 A | 2/2000 | Bardy |
| 6,034,295 A | 3/2000 | Rehberg et al. |
| 6,035,236 A | 3/2000 | Jarding et al. |
| 6,040,180 A | 3/2000 | Johe |
| 6,042,579 A | 3/2000 | Elsberry et al. |
| 6,052,624 A | 4/2000 | Mann |
| 6,055,456 A | 4/2000 | Gerber |
| 6,057,846 A | 5/2000 | Sever, Jr. |
| 6,057,847 A | 5/2000 | Jenkins |
| 6,058,331 A | 5/2000 | King |
| 6,060,048 A | 5/2000 | Cherksey |
| 6,061,593 A | 5/2000 | Fischell et al. |
| 6,066,163 A | 5/2000 | John |
| 6,095,148 A | 8/2000 | Shastri et al. |
| 6,104,956 A | 8/2000 | Naritoku et al. |
| 6,104,960 A | 8/2000 | Duysens et al. |
| 6,122,548 A | 9/2000 | Starkebaum et al. |
| 6,126,657 A | 10/2000 | Edwards et al. |
| 6,128,537 A | 10/2000 | Rise |
| 6,128,538 A | 10/2000 | Fischell et al. |
| 6,134,474 A | 10/2000 | Fischell |
| 6,152,143 A | 11/2000 | Edwards |
| 6,161,044 A | 12/2000 | Silverstone |
| 6,161,045 A | 12/2000 | Fischell et al. |
| 6,176,242 B1 | 1/2001 | Rise |
| 6,190,893 B1 | 2/2001 | Shastri et al. |
| 6,198,958 B1 | 3/2001 | Ives et al. |
| 6,205,360 B1 | 3/2001 | Carter et al. |
| 6,210,417 B1 * | 4/2001 | Baudino et al. ............. 606/129 |
| 6,221,908 B1 | 4/2001 | Kilgard et al. |
| 6,230,049 B1 | 5/2001 | Fischell et al. |
| 6,236,892 B1 | 5/2001 | Feler |

| | | |
|---|---|---|
| 6,246,912 B1 | 6/2001 | Sluijter et al. |
| 6,280,462 B1 | 8/2001 | Hauser et al. |
| 6,301,493 B1 | 10/2001 | Marro et al. |
| 6,319,241 B1 | 11/2001 | King et al. |
| 6,339,725 B1 | 1/2002 | Naritoku et al. |
| 6,353,754 B1 | 3/2002 | Fischell |
| 6,354,299 B1 | 3/2002 | Fischell |
| 6,356,792 B1 * | 3/2002 | Errico et al. ............ 607/116 |
| 6,360,122 B1 | 3/2002 | Fischell |
| 6,366,813 B1 | 4/2002 | DiLorenzo |
| 6,375,666 B1 | 4/2002 | Mische |
| 6,405,079 B1 | 6/2002 | Ansarinia |
| 6,418,344 B1 | 7/2002 | Rezai et al. |
| 6,427,086 B1 | 7/2002 | Fischell |
| 6,456,886 B1 | 9/2002 | Howard, III et al. |
| 6,459,936 B2 | 10/2002 | Fischell |
| 6,463,328 B1 | 10/2002 | John |
| 6,464,356 B1 | 10/2002 | Sabel |
| 6,466,822 B1 | 10/2002 | Pless |
| 6,473,639 B1 | 10/2002 | Fischell |
| 6,480,743 B1 | 11/2002 | Kirkpatrick |
| 6,484,059 B2 | 11/2002 | Gielen |
| 6,487,450 B1 | 11/2002 | Chen |
| 6,499,488 B1 | 12/2002 | Hunter et al. |
| 6,505,075 B1 | 1/2003 | Weiner |
| 6,507,755 B1 | 1/2003 | Gozani et al. |
| 6,529,774 B1 | 3/2003 | Greene |
| 6,539,263 B1 | 3/2003 | Schiff et al. |
| 6,556,868 B2 | 4/2003 | Naritoku et al. |
| 6,569,654 B2 | 5/2003 | Shastri et al. |
| 6,591,138 B1 | 7/2003 | Fischell et al. |
| 6,597,954 B1 | 7/2003 | Pless et al. |
| 6,615,065 B1 | 9/2003 | Barrett et al. |
| 6,622,048 B1 | 9/2003 | Mann |
| 6,633,780 B1 | 10/2003 | Berger |
| 6,647,296 B2 | 11/2003 | Fischell et al. |
| 6,658,299 B1 | 12/2003 | Dobelle |
| 6,665,562 B2 | 12/2003 | Gluckman et al. |
| 6,684,105 B2 | 1/2004 | Cohen et al. |
| 6,687,525 B2 | 2/2004 | Llinas |
| 6,690,974 B2 | 2/2004 | Archer et al. |
| 6,708,064 B2 | 3/2004 | Rezai |
| 6,725,094 B2 | 4/2004 | Saberski |
| 6,764,498 B2 | 7/2004 | Mische |
| 6,782,292 B2 | 8/2004 | Whitehurst |
| 6,788,975 B1 | 9/2004 | Whitehurst et al. |
| 6,795,737 B2 | 9/2004 | Gielen et al. |
| 6,810,286 B2 | 10/2004 | Donovan et al. |
| 6,839,594 B2 | 1/2005 | Cohen et al. |
| 6,873,872 B2 | 3/2005 | Gluckman et al. |
| 6,892,097 B2 | 5/2005 | Holsheimer |
| 6,895,280 B2 | 5/2005 | Meadows et al. |
| 6,907,296 B1 | 6/2005 | Doan et al. |
| 6,934,580 B1 | 8/2005 | Osorio et al. |
| 6,944,497 B2 | 9/2005 | Stypulkowski |
| 6,944,501 B1 | 9/2005 | Pless |
| 6,959,215 B2 | 10/2005 | Gliner et al. |
| 6,990,377 B2 | 1/2006 | Gliner et al. |
| 7,006,859 B1 | 2/2006 | Osorio et al. |
| 7,010,351 B2 | 3/2006 | Firlik et al. |
| 7,024,247 B2 | 4/2006 | Gliner et al. |
| 7,110,820 B2 | 9/2006 | Tcheng et al. |
| 2002/0077670 A1 | 6/2002 | Archer |
| 2002/0087201 A1 | 7/2002 | Firlik et al. |
| 2002/0091419 A1 | 7/2002 | Firlik |
| 2002/0099412 A1 | 7/2002 | Fischell |
| 2002/0169485 A1 | 11/2002 | Pless |
| 2003/0074032 A1 | 4/2003 | Gliner |
| 2003/0078633 A1 | 4/2003 | Firlik et al. |
| 2003/0088274 A1 | 5/2003 | Gliner et al. |
| 2003/0097161 A1 | 5/2003 | Firlik et al. |
| 2003/0114886 A1 | 6/2003 | Gluckman et al. |
| 2003/0125772 A1 | 7/2003 | Olson et al. |
| 2003/0125786 A1 | 7/2003 | Gliner et al. |
| 2003/0130706 A1 | 7/2003 | Sheffield et al. |
| 2003/0149457 A1 | 8/2003 | Tcheng et al. |
| 2003/0176901 A1 | 9/2003 | May |
| 2003/0187490 A1 | 10/2003 | Gliner |
| 2003/0187491 A1 | 10/2003 | Greenberg et al. |
| 2004/0073270 A1 | 4/2004 | Firlik et al. |
| 2004/0082847 A1 | 4/2004 | McDermott |
| 2004/0088024 A1 | 5/2004 | Firlik et al. |
| 2004/0092809 A1 | 5/2004 | Decharms |
| 2004/0102828 A1 | 5/2004 | Lowry et al. |
| 2004/0111127 A1 | 6/2004 | Gliner et al. |
| 2004/0131998 A1 | 7/2004 | Marom et al. |
| 2004/0138550 A1 | 7/2004 | Hartlep et al. |
| 2004/0158298 A1 | 8/2004 | Gliner |
| 2004/0176831 A1 | 9/2004 | Gliner et al. |
| 2004/0181263 A1 | 9/2004 | Balzer et al. |
| 2004/0215287 A1 | 10/2004 | Swoyer et al. |
| 2004/0236388 A1 | 11/2004 | Gielen et al. |
| 2004/0243205 A1 | 12/2004 | Keravel et al. |
| 2004/0249422 A1 | 12/2004 | Gliner et al. |
| 2005/0004620 A1 | 1/2005 | Singhal et al. |
| 2005/0015129 A1 | 1/2005 | Mische |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0033378 A1 | 2/2005 | Sheffield et al. |
| 2005/0070971 A1 | 3/2005 | Fowler et al. |
| 2005/0075679 A1 | 4/2005 | Gliner et al. |
| 2005/0075680 A1 | 4/2005 | Lowry et al. |
| 2005/0096701 A1 | 5/2005 | Donovan et al. |
| 2005/0113882 A1 | 5/2005 | Cameron et al. |
| 2005/0119712 A1 | 6/2005 | Shafer |
| 2005/0154425 A1 | 7/2005 | Boveja et al. |
| 2005/0154426 A1 | 7/2005 | Boveja et al. |
| 2005/0182453 A1 | 8/2005 | Whitehurst |
| 2006/0015153 A1 | 1/2006 | Gliner et al. |
| 2006/0106430 A1 | 5/2006 | Fowler et al. |
| 2006/0106431 A1 | 5/2006 | Wyler et al. |
| 2006/0129205 A1 | 6/2006 | Boveja et al. |
| 2006/0173522 A1 | 8/2006 | Osorio |
| 2006/0217782 A1 | 9/2006 | Boveja et al. |
| 2006/0241717 A1 | 10/2006 | Whitehurst et al. |

FOREIGN PATENT DOCUMENTS

| | | |
|---|---|---|
| EP | 0214527 | 3/1987 |
| EP | 0319844 A1 | 6/1989 |
| EP | 0 998 958 A2 | 10/2000 |
| EP | 1 145 736 | 10/2001 |
| EP | 1180056 | 11/2003 |
| WO | WO 86/07543 | 12/1986 |
| WO | WO 97/29708 | 8/1987 |
| WO | WO-87/07511 | 12/1987 |
| WO | WO-94/07564 | 4/1994 |
| WO | WO-95/21591 | 8/1995 |
| WO | WO-98/06342 | 2/1998 |
| WO | WO 99/34754 | 7/1999 |
| WO | WO 00/13743 | 3/2000 |
| WO | WO 01/00097 | 1/2001 |
| WO | WO-01/97906 | 12/2001 |
| WO | WO-02/09811 | 2/2002 |
| WO | WO-02/36003 | 5/2002 |
| WO | WO-02/38031 | 5/2002 |
| WO | WO-02/38217 | 5/2002 |
| WO | WO-03/082402 | 3/2003 |

| | | | |
|---|---|---|---|
| WO | WO-03/043690 | 5/2003 | |

OTHER PUBLICATIONS

Ross, Donald A., M.D., et al., "A Percutaneous Epidural Screw Electrode for Intracranial Electroencephalogram Recordings Technical Note," Neurosurgery, Aug. 1993, 5 pgs, vol. 33, No. 2.

Barr, Deborah et al., "Induction and Reversal of Long-Term Potentiation by Low- and High- Intensity Theta Pattern Stimulation," The Journal of Neuroscience, 15(7): pp. 5402-5410 (Jul. 1995).

Behrens, T. et al., "Non-invasive mapping of connections between human thalamus and cortex using diffusion imaging," Nature Neuroscience, vol. 6 No. 7, pp. 750-757 (Jul. 2003).

Bel, S. and Bauer, B.L., "Dorsal Column Stimulation (DCS): Cost to Benefit Analysis," Acta Neurochirurgica, Suppl. 52, pp. 121-123 (1991).

Benabid, A.L. et al, "Chronic electrical stimulation of the ventralis intermedius nucleus of the thalamus as a treatment of movement disorders," J. Neurosurg., Apr. 1997, 86(4); 737; http://www.ncbi.nlm.nih.gov; [accessed Nov. 18, 2003].

Bluestone, Avraham Y. et al., "Three-dimensional optical tomography of hemodynamics in the human head," Optics Express, vol. 9, No. 6, pp. 272-286 (Sep. 10, 2001).

Brain Electrical Stimulation to Enhance Recovery After Stroke. ClinicalTrials.gov. [Retrieved on Dec. 22, 2005]. Retrieved from the internet <URL http://www.clinicaltrials.gov/ct/show/NCT00085657?order=2>.

Burnett, Mark G. et al., "Diffuse optical measurement of blood flow, blood oxygenation, and metabolism in a human brain during sensorimotor cortex activation," Optics Letters, vol. 29, No. 15, pp. 1766-1768 (Aug. 1, 2004).

Butefisch et al., "Mechanisms of use-dependent plasticity in the human motor cortex," Proc. Natl. Acad. Sci. USA, vol. 97, No. 7, pp. 3661-3665 (Mar. 2000).

Canavero, S. and Paolotti, R., "Extradural Motor Cortex Stimulation afor Advanced Parkinson's Disease: Case Report," Movement Disorders, 15(1):169-171,2000.

Cao, Yue et al., "Cortical Language Activation in Stroke Patients Recovering From Aphasia With Functional MRI," Stroke, vol. 30, pp. 2331-2340, Nov. 1999.

Cincotta et al., "Reorganization of the motor cortex in a patient with congenital hemiparesis and mirror movements," Neurology, vol. 55, pp. 129-131 (2000).

Classen, et al., "Rapid Plasticity of Human Cortical Movement Representation Induced by Practice," The Journal of Neurophysiology, vol. 79, No. 2, pp. 1117-1123 (Feb. 1998).

Cohen et al., "Studies of Neuroplasticity With Transcranial Magnetic Stimulation," The Journal of Clinical Neurophysiology, vol. 15, No. 4 (1998).

Cramer, S.C. and Bastings, E.P., "Mapping clinically relevant plasticity after stroke," Neuropharmacology vol. 19, No. 5, pp. 842-851 (Apr. 2000).

Cytokines Web Clinical Significance. Cytokines Web, 2 pages. [Retrieved on Sep. 2, 2005]. Retrieved from the internet: <URL: http://cmbi.bjmu.edu.cn/cmbidata/cgf/CGF_Database/cytweb/roles/index.html>.

Dam et al., "Effects of Fluoxetine and Maprotiline on Functional Recovery in Poststroke Hemiplegic Patients Undergoing Rehabilitation Therapy," Stroke, vol. 27, No. 7, pp. 1211-1214 (Jul. 1996).

De Ridder, Dirk et al., "Magnetic and electrical stimulation of the auditory cortex for intractable tinnitus," Journal Neurosurg., vol. 100, pp. 560-564, (Mar. 2004).

Di Lazzaro, V. et al., "Theta-burst repetitive transcranial magnetic stimulation suppressess specific excitatory circuits in the human motor cortex," Physiology in Press; published online on Apr. 21, 2005 as 10.1113/jphysio.2005.087288.

Ding, Yuemin et al., "Neural Plasticity After Spinal Cord Injury," Current Pharmaceutical Design vol. 11, No. 11, pp. 1441-1450, Abstract Only- 1 page (Apr. 2005).

Duncan, Pamela W. et al., "Defining post-stroke recovery: implications for design and interpretation of drug trials," Neuropharmacology vol. 39, pp. 835-841 (2000).

Feys et al., "Value of somatosensory and motor evoked potentials in predicting arm recovery after a stroke," (Oct. 1999).

Franzini et al., "Reversal of thalamic hand syndrome by long-term motor cortex stimulation," Journal of Neurosurgery 93:873-875 (2000).

Fregni, Felipe et al., "Anodal Transcranial Direct Current Stimulation of Prefrontal Cortex Enhances Working Memory," Experimental Brain Research vol. 166, No. 1, pp. 23-30 (Sep. 2005).

Gladstone et al., "Enhancing Recovery after Stroke with Noradrenergic Pharmacotherapy: A New Frontier?," Can J. Neurol. Sci., vol. 27, No. 2 (May 2000).

Gordon et al., "Parameters for direct cortical electrical stimulation in the human: histopathologic confirmation," Electroencephalography and clinical neurophysiology, vol. 75, pp. 371-377 (1990).

Hagemann, Georg et al., "Increased Long-Term Potentiation in the Surround of Experimentally Induced Focal Cortical Infarction," Annals of Neurology, vol. 44, No. 2, pp. 255-258 (Aug. 1998).

Hayakawa, Toshiji et al., "Changes in Cerebral Oxygenation and Hemodynamics During Obstructive Sleep Apneas," Chest, vol. 109, pp. 916-921 (1996).

Hodge, Jr., C.J. and Boakye, M., "Biological Plasticity: The Future of Science in Neurosurgery," Neurosurgery, vol. 48, No. 1 (Jan. 2001).

Hoshi, Yoko et al., "Detection of dynamic changes in cerebral oxygenation coupled to neuronal function during mental work in a man," Neuroscience Letters, vol. 150, pp. 5-8 (1993).

Hoshino et al., "Application of multichannel near-infrared spectroscopic topography to physiological monitoring of the cortex during cortical mapping: technical case report," Surgical Neurology, vol. 64, pp. 272-275 (2005).

How Imagent™ Works. ISS Inc., 1 page [Retrieved on Oct. 14, 2005]. Retrieved from the internet: <URL http://www.iss.com/Products/imagent_fmri.html>.

Huang, Ying-Zu et al., "Theta Burst Stimulation of the Human Motor Cortex," Neuron, vol. 45, pp. 201-206 (Jan. 20, 2005).

Hummel, Friedhelm et al., "Effects of non-invasive cortical stimulation on skilld motor function in chronic stroke," Brain Advance Access, Jan. 5, 2005, pp. 1-10, Brain.

Imagent™ Functional Brain Imaging System. ISS, Inc., 2 pages [Retrieved on Oct. 14, 2005]. Retrieved from the internet: <URL http://www.iss.com/Products/imagent.html>.

Imagent™ functional Near Infrared Imaging System (fNIRS) Brain Imaging Using Infrared Photons. ISS Inc., 8 pages [Retrieved on Oct. 14, 2005]. Retrieved from the internet: <URL http://www.iss.com/products/imagent/Imagent.pdf>.

International Search Report for PCT/US03/37855; Apr. 29, 2004; Applicant: Northstar Neuroscience, Inc., 5 pages.

Janicek, Milos J. et al., "Dynamic Infrared Imaging of Newly Diagnosed Malignant Lymphoma Compared with Gallium-67 and Fluorine-18 Fluorodeoxyglucose (FDG) Positron Emission Tomography," Technology in Cancer Research and Treatment, vol. 2, No. 6, pp. 571-577 (Dec. 2003).

Kauhanen et al., "Domans and Determinants of Quality of Life After Stroke Caused by Brian Infarction," Arch. Phys. Med. Rehabil., vol. 81, pp. 1541-1546 (Dec. 2000).

Kilgard, Michael et al., "Cortical Map Reorganization Enabled by Nucleus Basalis Activity," Science, vol. 279 pp. 1714-1717 (Mar. 13, 1998).

Kopell et al., "The Continuing Evolution of Psychiatric Neurosurgery," CNS Spectrums, vol. 5, No. 10, pp. 20-31 (Oct. 2000).

L-DOPA dyskinesias. BioChemistry of PD. [Retrieved on Dec. 22, 2005]. Retrieved from the internet <URL <http://www.mayo.edu/fdp/pd-info/dyskinesias.htm>>.

Lang, Nicolas et al., "Preconditioning with Transcranial Direct Current Stimulation Sensitizes the Motor Cortex to Rapid-Rate Transcranial Magnetic Stimulation and Controls and Direction of After-Effects," Biol Psychiatry 2004:56:634-639, 2004 Society of Biological Psychiatry.

Larson, John et al., "Reversal of LTP by theta frequency stimulation," Brain Research, 600: pp. 97-102 (1993).

Lazar, M. et al., "White Matter Tractography Using Diffusion Tensor Deflection," Human Brain Mapping, 18:306-321, (2003).

Levy et al., "Functional MRI Evidence of Cortical Reorganization in Upper-Limb Stroke Hemiplegia Treated with Constraint-Induced Movement Therapy," American Journal of Physical Medicine & Rehabilitation, vol. 80, No. 1, pp. 4-7 (2001).

Liepert et al., "Treatment-Induced Cortical Reorganization After Stroke in Humans," Stroke, 31:1210-1216 (2000).

Malenka, R.C. and Nicoll, R.A., "Long-Term Potenetiation—A Decade of Progress?," Neuroscience, vol. 285, No. 5435, Issue of Sep. 17, 1999, pp. 1870-1874.

Mansur, C.G., et al., "A sham stimulation-controlled trial of rTMS of the unaffected hemisphere in stroke patients," Neurology, vol. 64, pp. 1802-1804 (2005).

Martin et al, "Transcranial Magnetic Stimulation as a Complementary Treatment for Aphasia," Semin Speech Language, vol. 25, pp. 181-191 (2004) Abstract Only- 1 page.

Martinez et al., "Motor hand recovery after stroke Prognostic yield of early transcranial magnetic stimulation," Electromyography. Clin. Neurophysiology, vol. 39, pp. 405-410 (1999).

Meyerson, B.A. et al., "Motor Cortex Stimulation as Treatment of Trigeminal Neuropathic Pain", Acta Neurochirurgica Supplementum, vol. 58, pp. 150-153 (1993).

Netz et al., "Reorganization of motor output in the non-affected hemisphere after stroke," Brain, 120, pp. 1579-1586 (1997).

Nitsche, M.A. and Paulus, W., "Excitability changes induced in the human motor cortex by weak transcranial direct current stimulation," The Journal of Physiology, vol. 527.3, pp. 663-639 (2000).

Nitsche, Michael A. et al., "Level of action of cathodal DC polarisation induced inhibition of the human motor cortex," Dec. 2, 2002, Clinical Neurophysiology 114 (2003) 600-604.

Nitsche, Michael A., et al. "Facilitation of Implicit Motor Learning by Weak Transcranial Direct Current Stimulation of the Primary Motor Cortex in the Human," Journal of Cognitive Neuroscience 15:4, pp. 619-626, 2003 Massachusetts Institute of Technology.

Oliveri et al., "Paired transcranial magnetic stimulation protocols reveal a pattern of inhibition and facilitation in the human parietal cortex," The Journal of Physiology, 529.2, pp. 461-468 (2000).

Panchanathan, Sethuraman et al., "Rehabilitation of patients with hemispatial neglect using visual-haptic feedback in Virtual reality environment," [Retrieved on Dec. 22, 2005]. Retrieved from the internet <URL <http://www.public.asu.edu/~tmcdani/publications.htm>>.

Pascual-Leone et al., "Study and Modulation of Human Cortical Excitability With Transcranial Magnetic Stimulation," Journal of Clinical Neurophysiology, vol. 15, No. 4 (1998).

Pascual-Leone et al., "Transcranial magnetic stimulation and neuroplasticity," Neurophycologia 37, pp. 207-217 (1999).

Paulus, W, "Supplements to Clinical Neurophysiology," Transcranial Magnetic Stimulation and Transcranial Direct Current Stimulation (Supplements to Clinical Neurophysiology; vol. 56), pp. 249-254, 2003 Elsevier Science, B.V.

Paulus, Walter, "Toward Establishing a Therapeutic Window for rTMS by Theta Burst Stimulation," Neuron, vol. 45, pp. 181-183 (Jan. 20, 2005).

Penn, Michael, "Stemming Parkinson's," On Wisconsin Alumni Magazine, Summer 2003, [Retrieved on Dec. 22, 2005]. Retrieved from the internet <URL http://www.uwalumni.com/onwisconsin/2003_summer/research.html>.

Rezai, "Neurostimulation," Neurological Research, vol. 22, No. 3 pp. 235-273 (Apr. 2000).

Rossi et al., "Effects of Repetitive Transcranial Magnetic Stimulation on Movement-related Cortical Activity in Humans," Cerebral Cortex, vol. 10, No. 8, pp. 802-808 (Aug. 2000).

Roux et al., "Chronic Motor Cortex Stimulation for Phantom Limb Pain: A Functional Magnetic Resonance Imagining Study: Technical Cast Report," Neurosurgery, vol. 49, No. 3 (Mar. 2001).

Saitou et al., "Cerebral Blood Volume and Oxygenation Among Poststroke Hemiplegic Patients: Effects of 13 Rehabilitation Tasks Measured by Near-Infrared Spectroscopy," Arch. Phys. Med. Rehabil., vol. 81 pp. 1348-1356 (Oct. 2000).

Sandkuhler, "Learning and memory in pain pathways," Pain 88, pp. 113-118 (2000).

Sanes, "The Relation between Human Brain Activity and Hand Movements," NeuroImage 11, pp. 370-374 (2000).

Sanes, J. and Donoghue, J.P., "Plasticity and Primary Motor Cortex," Annual Review of Neuroscience 23:393-415 (2000).

Schaefer, Pamela W. et al., "Assessing Tissue Viability with MR Diffusion and Perfusion Imaging," AJNR, 24: pp. 436-443 (Mar. 2003).

Schiene, Klaus et al., "Neuronal Hyperexcitability and Reduction of GABA-Receptor Expression in the Surround of Cerebral Photothrombosis," Journal of Cerebral Blood Flow and Metabolism, vol. 16, No. 5, pp. 906-914 (1996).

Schiff et al., "A neuromodulation strategy for rational therapy of complex brain injury states," Neurological Research, vol. 22 pp. 267-272 (Apr. 2000).

SCIRun. Scientific Computing and Imaging Institute, 2 pages. [Retrieved on Jul. 24, 2005]. Retrieved from the Internet: <URL: http://sofware.sci.utah.edu/scirun.html>.

Shimizu et al., "Therapeutic efficacy of transcranial magnetic stimulation for hereditary spinocerebellar degeneration," Tohoku Journal of Experimental Medicine, 189(3):203-11 (Nov. 1999).

Siebner et al., "Lasting cortical activation after repetitive TMS of the motor cortex," NEUROLOGY 54, pp. 956-963 (Feb. 2000).

Stefan et al., "Introduction of plasticity in the human motor cortex by paired associative stimulation," Brian, vol. 123, No. 3, pp. 575-584 (Mar. 2000).

Strangman, Gary et al., "A Quantitative Comparison of Simultaneous BOLD fMRI and NIRS Recordings during Functional Brain Activation," NeuroImage, vol. 17, pp. 719-731 (2002).

Strangman, Gary et al., "Factors affecting the accuracy of near-infrared spectroscopy concentration calculations for focal changes in oxygenation parameters," NeuroImage, vol. 18, pp. 865-879 (2003).

Strangman, Gary et al., "Non-Invasive Neuroimaging Using Near-Infrared Light," Biological Psychiatry, vol. 52, pp. 679-693 (2002).

Strens, Lucy et al., "The ipsilateral Human Motor Cortex Can Functionally Compensate for Acute Contralateral Motor Cortex Dysfunction," Current Biology, vol. 13, pp. 1201-1205 (Jul. 15, 2003).

Taga, Gentaro et al., "Brain imaging in awake infants by near-infrared optical topogrpahy," PNAS, vol. 100, No. 19, pp. 10722-10727 (Sep. 16, 2003).

Tang, Cha-Min et al., "Optical Coherence Tomography of the Human Basal Ganglion," Deep Brain Stimulation Consortium Meeting Program Book, Sep. 29-30, 2003, Washington DC.

The GES 250 for Dense-Array EEG Research. Electrical Geodesics, Inc., 3 pages. [Retrieved on Aug. 25, 2005]. Retrieved from the internet: <URL: http://www.egi.com/ges250r_n.html>.

The INVOS Cerebral Oximeter. Somanetics, 1 page [Retrieved on Dec. 22, 2005]. Retrieved from the internet <URL <http://www.somanetics.net/invos.htm>>.

Theoret, Hugo et al., "Exploring Paradoxical Functional Facilitation with TMS," Supplements to Clinical Neurophysiology, vol. 56, pp. 211-219 (2003).

Thomas, Carmen et al., "Do Children with aggressive behavior have temporal lobe changes?" Alasbimn Journal, Year 5, No. 19, 8 pages (Jan. 2003).

Timmermann, Lars et al., "The cerebral oscillatory network of parkinsonian resting tremor," Brain, vol. 126, pp. 199-212, (2003).

Toronov, Vlad et al., "Near-infrared study of fluctuations in cerebral hemodynamics during rest and motor stimulation: Temporal analysis and spatial mapping," Medical Physics, vol. 27, No. 4, pp. 801-815 (Apr. 2000).

Tractography. Absolute Astronomy Reference, 2 pages. [Retrieved on Jul. 24, 2005]. Retrieved from the internet: <URL: http://www.absoluteastronomy.com/encyclopedia/T/Tr/Tractography.htm>.

Tsubokawa, T. et al., "Chronic Motor Cortex Stimulation for the Treatement of Central Pain", Acta Neurochirurgica Supplementum, vol. 52, pp. 137-139 (1991).

Tsubokawa, T. et al., "Treatment of Thalamic Pain by Chronic Motor Cortex Stimulation", PACE, vol. 14, pp. 131-134 (Jan. 1991).

Tsubokawa, T., "Chronic Motor Cortex Stimulation in Patients with Thalamic Pain," J. Neurosurg 78:393-401, (Mar. 1993).

Tuch, D. et al., "Conductivity Tensor Mapping of the Human Brain Using Diffusion Tensor MRI," Neurobiology, vol. 98 No. 20, pp. 11697-11701 (Sep. 25, 2001).

Turton et al., "Contralateral and ipsilateral EMG responses to transcranial magnetic stimulation during recovery of arm and hand function after stroke," Electroencephalography and Clinical Neurophysiology 101 pp. 316-328 (1996).

Turton, A. and Lemon, R.N., "The contribution of fast corticospinal input to the voluntary activation of proximal muscles in normal subjects and in stroke patients," Exp. Brain Res., vol. 129, pp. 559-572 (1999).

Van Der Lee et al., "The Intra- and Interrater Reliability of the Action Research Arm Test: A Practical Test of Upper Extremity Function in Patients With Stroke," Arch. Phys. Med. Rehabil., vol. 82 pp. 14-19 (Jan. 2001).

Walker-Batson et al., "Amphetamine Paired With Physical Therapy Accelerates Motor Recovery After Stroke," Stroke, vol. 26, No. 12, pp. 2254-2259 (1995).

Weinand, Martin E. et al., "Cerebral blood flow and temporal lobe epileptogenicity," [Retrieved on Dec. 22, 2005]. Retrieved from the internet: <URL http://www.aans.org/education/journal/neurosurgical/nov96/1-5-3.asp>.

Yokoh, Arika et al., "Intermittent versus continuous brain retraction," Journal of Neurosurgery, vol. 58, pp. 918-923 (Jun. 1983).

Ziemann et al., "Modulation of Plasticity in Human Motor Cortex after Forearm Ischemic Nerve Block," The Journal of Neuroscience, vol. 18, No. 3, pp. 1115-1123 (Feb. 1998).

Barres et al., "Proliferation of oligodendrocyte precursor cells depends on electrical activity in axons," Nature; Medical Research Council Developmental Neurobiology Programme, Department of Biology, University College, London, pp. 258-260, Jan. 21, 1993.

Bury, Scott et al., "The Effects of Behavioral Demand on Motor Cortical and Cerebellar Structural Plasticity After Brain Injury in Adult Rats," [Retrieved on Mar. 1, 2003]. Retrieved from the internet: <URL: http://www.mcmaster.ca.inabis98/schallert/bury0827/index.html>.

Cheun et al., "Differentiation of a Stem Cell Line Toward a Neuronal Phenotype," Int. J. Devl. Neuroscience, vol. 9, No. 4, pp. 391-404, 1991.

Haglund, Michael M. et al., "Optical imaging of epileptiform and functional activity in human cerebral cortex," Nature, vol. 358, pp. 668-671, Aug. 20, 1992.

Ishibashi, Tomoko et al., "Astrocytes Promote Myelination in Response to Electrical Impulses," Neuron 49, pp. 823-832, Mar. 16, 2006.

Keyvani, Kathy et al., "Suppression of proteasome C2 contralateral to ischemic lesions in rat brain," Brain Research, vol. 858, pp. 386-392, 2000.

Nudo, Randolph J., et al., "Recovery after damage to motor cortical areas," Current Opinion in Neurobiology, vol. 9, Issue 6, pp. 740-747, Dec. 1, 1999.

Robinson, Kenneth R., "The Responses of Cells to Electrical Fields: A Review," The Journal of Cell Biology, vol. 101, pp. 2023-2027, Dec. 1985.

U.S. Appl. No. 10/583,630, filed Jun. 20, 2006, Lozano.
U.S. Appl. No. 11/254,060, filed Oct. 19, 2005, Wyler.
U.S. Appl. No. 11/254,240, filed Oct. 19, 2005, Wyler.
U.S. Appl. No. 11/255,187, filed Oct. 19, 2005, Firlik.
U.S. Appl. No. 11/344,453, filed Jan. 30, 2006, Gliner.
U.S. Appl. No. 11/518,139, filed Sep. 7, 2006, Weinand.
U.S. Appl. No. 11/583,349, filed Oct. 18, 2006, Sloan.
U.S. Appl. No. 11/638,326, filed Dec. 12, 2006, Gliner et al.
U.S. Appl. No. 11/697,694, filed Apr. 6, 2007, Fowler.
U.S. Appl. No. 11/697,696, filed Apr. 6, 2007, Pascual-Leone.
U.S. Appl. No. 11/697,703, filed Apr. 6, 2007, Gaw.

Beveridge, J. A., "Use of Exogenous Electric Current in the Treatment of Delayed Lesions in Peripheral Nerves;" Plastic and Reconstructive Surgery, Oct. 1988, vol. 82, No. 4, pp. 573-579.

Bezard et al., "Cortical Stimulation and Epileptic Seizure: A Study of the Potential Risk in Primates," Neurosurgery, vol. 45, No. 2, Aug. 1999, 346-350.

Binder, J. M.D., "Functional Magnetic Resonance Imaging: Language Mapping," Neurosurgery Clinics of North America, vol. 8, No. 3, Jul. 1997, pp. 383-392.

Cicinelli et al., "Transcranial magnetic stimulation reveals an interhemispheric asymmetry of cortical inhibition in focal epilepsy," Neurophysiology, vol. 11, No. 4 Mar. 20, 2000, pp. 701-707.

Cincotta et al., "Suprathreshold 0.3 Hz repetitive TMS prolongs the cortical silent period: potential implications for therapeutic trials in epilepsy," Clinical Neurophysiology, vol. 114, 2003, pp. 1827-1833, Elsevier Ireland Ltd.

CNN.com, Health, "Lab Zaps Strokes with Magnetic Pulses," http://www.cnn.com/2004/HEALTH/conditions/11/29/zapping.strokes.ap/, Nov. 29, 2004, 4 pages [Retrieved on Dec. 2, 2004].

Cramer et al., "Use of Functional MRI to Guide Decisions in a clinical Stroke Trial," Stroke, Journal of the American Heart Association, May 2005, pp. e50-e52, American Heart Association, Dallas TX.

Ferrari, A. et al., "Immature human NT2 cells grafted into mouse brain differentiate into neuronal and glial cell types," FEBS Letters, Dec. 8, 2000, pp. 121-125, vol. 486, No. 2, Elsevier Science B.V., Amsterdam.

Fregni et al., "Antiepileptic Effects of Repetitive Transcranial Magnetic Stimulation in Patients with Cortical Malformations: An EEG and Clinical Study," ASSFN Proceedings 2004, Stereotactic and Functional Neurosurgery, 2005, 83:57-62.

Velasco et al. "Absolute and Relative Predictor Values of Some Non-Invasive and Invasive Studies for the Outcome of Anterior Temporal Lobectormy," Science Direct, vol. 31, Issue 1, Jan.-Feb. 2000, pp. 62-74, Elsevier Science, Inc.

Velasco et al., "Acute and Chronic Electrical Stimulation of the Centromedian Thalamic Nucleus: Modulation of Reticulo-Cortical Systems and Predictor Factors for Generalized Seizure Control," Archives of Medical Research, vol. 31, 2000, pp. 304-315, Elsevier Science, Inc.

Velasco et al., "Electrical Stimulation for Epilepsy: Stimulation of Hippocampal Foci," Stereotactic and Functional Neurosurgery, vol. 77, 2001, pp. 223-227.

Velasco et al., "Subacute and Chronic Electrical Stimulation of the Hippocampus on Intractable Temporal Lobe Seizures: Preliminary Report," Archives of Medical Research, vol. 31, 2000, pp. 316-328, Elsevier Science, Inc.

Velasco et al., "Subacute Electrical Stimulation of the Hippocampus Blocks Intractable Temporal Lobe Seizures and Paroxysmal EEG Activities," Epilepsia, vol. 41, No. 2, 2000, pp. 158-169, Lippincott Williams & Wilkins, Philadelphia.

Waxman et al., "The Interictal Behavior Syndrome of Temporal Lobe Epilepsy," Arch Gen Psychiatry, vol. 32, Dec. 1975, pp. 1580-1586.

Weinand et al., "Cerebral blood flow and temporal lobe epileptogenicity," J Neurosurg, vol. 86, Feb. 1997, pp. 226-232.

Weinand et al., "Cerebral blood flow and temporal lobe epileptogenicity," Neurosurgical Focus, Nov. 1996, vol. 1, No. 5, AANS.ORG, http://www.aans.org/education/journal/neurosurgical/nov96/1-5-3.asp, 17 pages.

Weinand et al., Long-term ictal monitoring with subdural strip electrodes: prognostic factors for selecting temporal lobectomy candidates, J Neurosurg, vol. 77, 1992, pp. 20-28.

Weinand et al., "Surface cortical cerebral blood flow monitoring and single photon emission computed tomography: prognostic factors for selecting temportal lobectormy candidates," Seizure, vol. 3, 1994, pp. 55-59.

Weinand et al., "Targeted Subthreshold Cortical Stimulation for Recovery of Motor Hand Function following Hemiparetic Stroke," Abstract: Apr. 18, 2005 AANS.org, http://www.aans.org/Library/Article.aspx?ArticleId=24934, 2 pages.

Woodbury, D. et al., "Adult Rat and Human Bone Marrow Stromal Cells Differentiate Into Neurons," Journal of Neuroscience Research, 2000, vol. 61, pp. 364-370, Wiley Interscience, New York, NY.

Yamamoto et al., "Low-frequency Electric Cortical Stimulation Has an Inhibitory Effect on Epileptic Focus in Mesial Temporal Lobe Epilepsy," Epilepsia, vol. 43, No. 5, 2002, pp. 291-295, Blackwell Publishing, Inc.

Kelly-Spratt, K. "Transfection of PC-12 cells: a model system for primary neuronal cells. " Qiagen News, Customer application article, www.qiagen.com, Issue 4, 1998, 2 pages.

Kimura, K. et al., "Electrically induced neurite outgrowth of PC12 cells on the electrode surface," Entrez PubMed, http://www.ncbi.nlm.nih.gov/entrez/query.fcgi?db=pubmed&cmd=Retrieve&dopt=Abstract, 1 page.

Kinoshita et al., "Electric cortical stimulation suppresses epileptic and background activities in neocortical epilepsy and mesial temporal lobe epilepsy," Clinical Neurophysiology, vol. 116, 2005, pp. 1291-1299, Elsevier Ireland Ltd.

Kossoff et al., "Effect of an External Responsive Neurostimulator on Seizures and Electrographic Discharges during Subdural Electrode Monitoring," Epilepsia 45(12):1560-1567, 2004, Blackwell Publishing, Inc.

Lutsep et al., "Safety of Cortical Stimulation in Patients with Hemiparetic Stroke," Oasis, Online Abstract Submission and Invitation System - Program Planner, International Stroke Conference 2005, 1 pages, American Stroke Association.

Mendonca, A.C., "Directly applied low intensity direct electric current enhances peripheral nerve regeneration in rats," Journal of Neuroscience Methods, 2003, vol. 129, pp. 183-190.

Misawa et al., "Low-frequency transcranial magnetic stimulation for epilepsia partialis continua due to cortical dysplasia," Journal of the Neurological Sciences, vol. 234, 2005, pp. 37-39.

Montgomery, "Thalamic Stimulation," Neuroscience Pathways, The Cleveland Clinic Foundation, 2 pages.

Motamedi et al., "Optimizing Parameters for Terminating Cortical Afterdischarges with Pulse Stimulation," Epilepsia 43(8):836-846, 2002, Blackwell Publishing, Inc.

Politis, M. J., "Mammalian Optic Nerve Regeneration Following the Application of Electric Fields," The Journal of Trauma, Nov. 1988, vol. 28, No. 11, pp. 1548-1552.

Price, J. et al., "Neurotransplantation in neurodegenerative disease: a survey of relevant issues in developmental neurobiology," Novartis Foundation Symposium 231, 2000, pp. 148-165, Wiley, Chichester, UK.

Schulz et al., "Localization of Epileptic Auras Induced on Stimulation by Subdural Electrodes," Epilepsia, Dec. 1997, vol. 38, Issue 12, pp. 1321-1329.

Sioutos et al. Continuous Regional Cerebral Cortical Blood Flow Monitoring in Head-injured Patients, Neurosurgery, vol. 36, No. 5, May 1995, pp. 943-949.

Storer et al., "Microiontophoretic application of serotonin (5HT) 1B/1D agonists inhibits trigeminal cell firing in the cat," Brain, 1997, vol. 120, Issue 12, pp. 2171-2177, Oxford University Press.

Suzuki et al., "Selective Electrical Stimulation of Postganglionic Cerebrovascular Parasympathetic Nerve Fibers Originating from the Sphenopalatine Ganglion Enhances Cortical Blood Flow in the Rat," Journal of Cerebral Blood Flow and Metabolism, May 1990, 10(3):383-91.

The National Institutes of Health (NIH) Consensus Development Program, "Surgery for Epilepsy," National Institutes of Health Consensus Development conference Statement, Mar. 19-21, 1990, 16 pages.

* cited by examiner

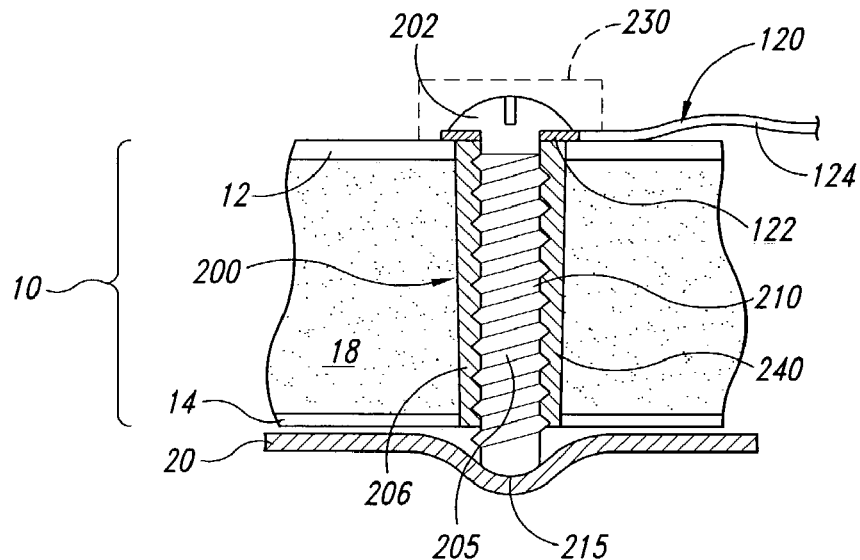
*Fig. 4A*
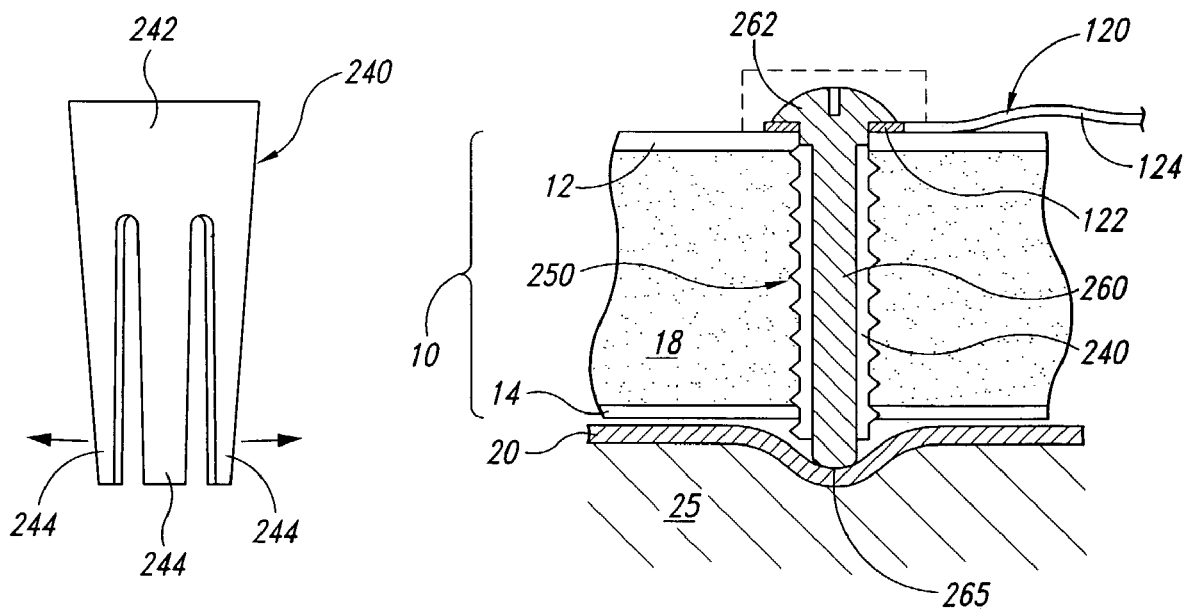
*Fig. 4B*          *Fig. 5*

METHODS AND SYSTEMS EMPLOYING INTRACRANIAL ELECTRODES FOR NEUROSTIMULATION AND/OR ELECTROENCEPHALOGRAPHY

RELATED APPLICATION

This application claims priority from Provisional Application Ser. No. 60/429,481, filed Nov. 27, 2002.

TECHNICAL FIELD

The present invention relates to intracranial electrodes and methods for implanting and using intracranial electrodes. These electrodes and methods are particularly well suited for neurostimulation systems and may also be used in electroencephalography and other recording systems, e.g., evoked potential recordings.

BACKGROUND

A wide variety of mental and physical processes are known to be controlled or influenced by neural activity in the central and peripheral nervous systems. For example, the neural functions in some areas of the brain (e.g., the sensory or motor cortices) are organized according to physical or cognitive functions. Several other areas of the brain also appear to have distinct functions in most individuals. In the majority of people, for example, the areas of the occipital lobes relate to vision, the regions of the left inferior frontal lobes relate to language, and the regions of the cerebral cortex appear to be involved with conscious awareness, memory, and intellect. Because of the location-specific functional organization of the brain, in which neurons at discrete locations are statistically likely to control particular mental or physical functions in normal individuals, stimulating neurons at selected locations of the central nervous system can be used to effectuate changes in cognitive and/or motor functions throughout the body.

In several existing applications, neural functions are treated or augmented by electrical or magnetic stimulation powered by a neural stimulator that has a plurality of therapy electrodes and a pulse system coupled to the therapy electrodes. The therapy electrodes can be implanted into the patient at a target site for stimulating the desired portions of the brain. For example, one existing technique for masking pain in a patient is to apply an electrical stimulus to a target stimulation site of the brain. In other applications, transcranial magnetic stimulation (TMS) of an appropriate target site in the brain has shown promise for treating damage to and disease and disorders of the brain, including depression and, possibly, obsessive-compulsive behavior.

The brain can be stimulated in several known fashions. One type of treatment is referred to as transcranial electrical stimulation (TES), which involves placing an electrode on the exterior of the patient's scalp and delivering an electrical current to the brain through the scalp and the skull. TES, however, is not widely used because the delivery of the electrical stimulation through the scalp and the skull causes patients a great amount of pain and the electrical field is difficult to direct or focus accurately.

Another type of treatment is the transcranial magnetic stimulation (TMS) identified above. TMS, involves using a high-powered magnetic field adjacent the exterior of the scalp over an area of the cortex. TMS does not cause the painful side effects of TES. Unfortunately, TMS is not presently effective for treating many patients because the existing delivery systems are not practical for applying stimulation over an adequate period of time. TMS systems, for example, are relatively complex and require stimulation treatments to be performed by a healthcare professional in a hospital or physician's office. The efficacy of TMS in longer-term therapies may be limited because it is difficult to (a) accurately localize the region of stimulation in a reproducible manner, (b) hold the device in the correct position over the cranium for the requisite period, and (c) provide stimulation for extended periods of time.

Another device for stimulating a region of the brain is disclosed by King in U.S. Pat. No. 5,713,922, the entirety of which is incorporated herein by reference. King discloses a device for cortical surface stimulation having electrodes mounted on a paddle that is implanted under the skull of the patient. These electrodes are placed in contact with the surface of the cortex to create "paresthesia," which is a vibrating or buzzing sensation. Implanting the paddle typically requires removal of a relatively large (e.g., thumbnail-sized or larger) window in the skull via a full craniotomy. Craniotomies are performed under a general anesthetic and subject the patient to increased chances of infection.

A physician may employ electroencephalography (EEG) to monitor neural functions of a patient. Sometimes this is done alone, e.g., in diagnosing epileptic conditions, though it may also be used in conjunction with neurostimulation. Most commonly, electroencephalography involves monitoring electrical activity of the brain, manifested as potential differences at the scalp surfaces, using electrodes placed on the scalp. The electrodes are typically coupled to an electroencephalograph to generate an electroencephalogram. Diagnosis of some neurological diseases and disorders, e.g., epilepsy, may best be conducted by monitoring neural function over an extended period of time. For this reason, ambulatory electroencephalography (AEEG) monitoring is becoming more popular. In AEEG applications, disc electrodes are applied to the patient's scalp. The scalp with the attached electrodes may be wrapped in gauze and the lead wires attached to the electrodes may be taped to the patient's scalp to minimize the chance of displacement.

EEG conducted with scalp-positioned electrodes requires amplification of the signals detected by the electrodes. In some circumstances, it can be difficult to pinpoint the origin of a particular signal because of the signal dissipation attributable to the scalp and the skull. For more precise determinations, EEG may be conducted using "deep brain" electrodes. Such electrodes extend through the patient's scalp and skull to a target location within the patient's brain. Typically, these deep brain electrodes comprise lengths of relatively thin wire that are advanced through a bore through the patient's skull to the desired location. If the electrodes are to be monitored over an extended period of time, the electrodes typically are allowed to extend out of the patient's skull and scalp and are coupled to the electroencephalograph using leads clipped or otherwise attached to the electrodes outside the scalp. To avoid shifting of the electrodes over time, the electrodes typically are taped down or held in place with a biocompatible cementitious material. The patient's head typically must be wrapped in gauze to protect the exposed electrodes and the associated leads, and the patient is uncomfortable during the procedure. This may be suitable for limited testing purposes-deep brain encephalography typically is limited to tests conducted in hospital settings over a limited period of time, usually no more than a few days—but could be problematic for longer-term monitoring, particularly in nonclinical settings.

Screws have been used to attach plates or the like to patients' skulls. FIG. 1, for example, schematically illustrates a conventional cranial reconstruction to repair a fracture 50 or other trauma. In this application, a plate 60 is attached to the outer cortex 12 of the skull 10 by cortical bone screws 62. The plate 60 spans the fracture 50, helping fix the skull in place on opposite sides of the fracture 50. As can be seen in FIG. 1, the screws 62 do not extend through the entire thickness of the skull. Instead, the screws 62 are seated in the outer cortex 12 and do not extend into the cancellous 18 or the inter cortex 14. In some related applications, the screws 62 may be longer and extend into or even through the cancellous 18. Physicians typically take significant care to ensure that the screws 62 do not extend through the entire thickness of the skull, though, because penetrating the skull can increase the likelihood of trauma to or infection in the patient's brain.

BRIEF DESCRIPTION OF THE DRAWINGS

FIG. 4A is a schematic illustration in partial cross section of an intracranial electrode in accordance with yet another embodiment of the invention implanted in a patient.

FIG. 4B is a side view of a dielectric member of the electrode of FIG. 4A.

FIG. 5 is a schematic illustration in partial cross section of an intracranial electrode in accordance with still another embodiment of the invention implanted in a patient.

DETAILED DESCRIPTION

A. Overview

Figure 1:
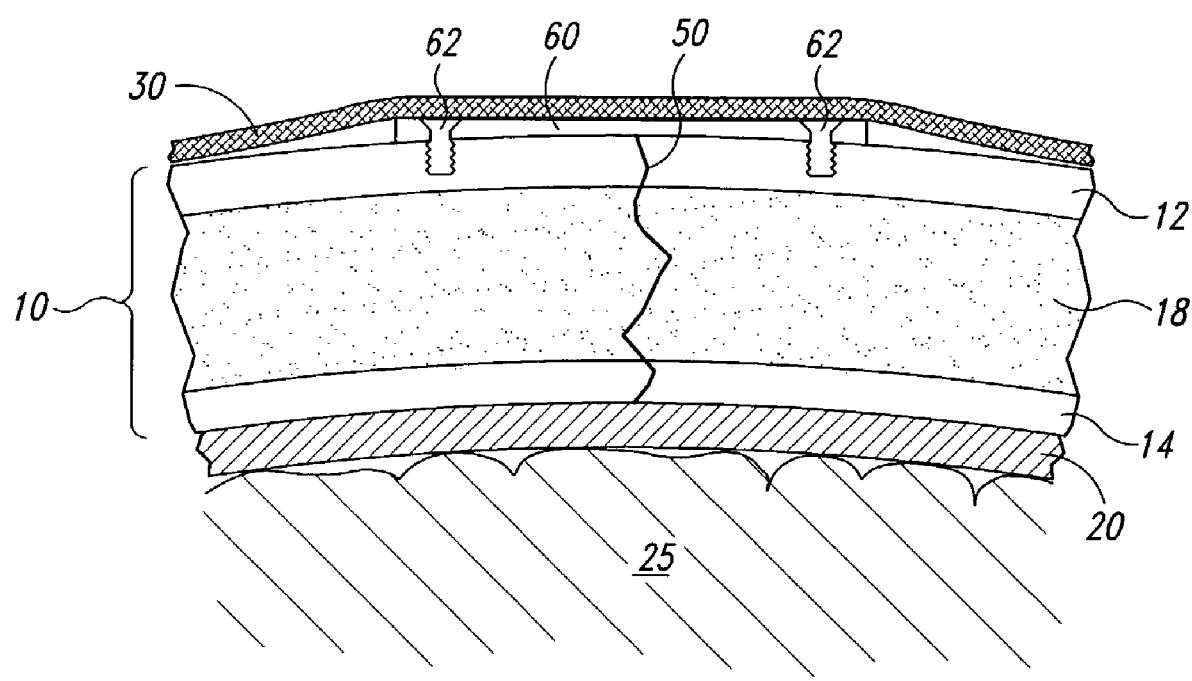
FIG. 1 is a schematic illustration of a conventional cranial reconstruction.

Various embodiments of the present invention provide intracranial electrodes and methods for implanting and using intracranial electrodes. It will be appreciated that several of the details set forth below are provided to describe the following embodiments in a manner sufficient to enable a person skilled in the art to make and use the disclosed embodiments. Several of the details and advantages described below, however, may not be necessary to practice certain embodiments of the invention. Additionally, the invention can also include additional embodiments that are not described in detail with respect to FIGS. 1-24.

One embodiment of the invention provides an intracranial electrode that includes a shaft, a head, and threads. The shaft includes a distal contact surface adapted to electrically contact a surface of a patient's brain. The head is associated with the shaft and is sized to be positioned subcutaneously adjacent the patient's skull. This can ameliorate the difficulties associated with electrodes that protrude through the patient's scalp, including irritation of the skin and discomfort. The threads are carried by at least one of the head and the shaft and may be adapted to fix the electrode with respect to the patient's skull. This intracranial electrode has an adjustable length adapted to change a contact force of the distal contact surface against the surface of the brain by adjusting the length of the electrode. In one adaptation of this embodiment, the intracranial electrode includes an adjustment means that is adapted to adjust the length of the electrode.

Another embodiment of the invention provides an intracranial electrode that includes an electrically conductive member, a dielectric member, and an anchor. The electrically conductive member has a blunt contact surface and the dielectric member has an interior in which the electrically conductive member is received. The anchor may be carried by the electrically conductive member or the dielectric member. The anchor is adapted to anchor at least one of the electrically conductive member and the dielectric member with respect to a patient's skull adjacent a brain surface such that the contact surface of the electrically conductive member is in electrical contact with the brain surface and the dielectric member electrically insulates the skull from the electrically conductive member.

Another embodiment of the invention provides a neurostimulator system. This neurostimulator system includes an intracranial electrode, a lead, and a pulse system. The intracranial electrode may take the form of one of the preceding embodiments. In one particular implementation, the intracranial electrode includes a shaft including a distal contact surface adapted to electrically contact a surface of a patient's brain; a head associated with the shaft, with the head being sized to be positioned subcutaneously adjacent the patient's skull; and threads carried by at least one of the head and the shaft, with the threads being adapted to fix the electrode with respect to the patient's skull. The lead is adapted to be subcutaneously implanted beneath the patient's scalp. The lead has a first portion, which is adapted to be electrically coupled to the contact surface, and an electrically insulated implantable length. The pulse system is adapted to be implanted in the patient's body at a location spaced from the electrode. The pulse system is operatively coupled to the electrode via the lead to deliver an electrical stimulus to the brain via the electrode. If so desired, an array of such intracranial electrodes may be employed and the pulse system may be adapted to generate an electrical potential between the electrodes in the array.

A method of implanting an intracranial electrode in accordance with another embodiment of the invention involves advancing a threaded electrode through a patient's skull until a contact surface of the electrode is in atraumatic contact with a surface of the patient's brain. The threaded electrode is electrically coupled to a lead. A head of the electrode and the length of the lead are covered with the patient's scalp, thereby enclosing the electrode. An electrical stimulus is delivered to the patient's brain via the electrode. This electrical stimulus may be generated by a pulse system electrically coupled to the electrode by the lead. In one adaptation of this embodiment, the method may also include adjusting a length of the electrode, e.g., to adjust the force of the contact surface of the electrode against the surface of the brain.

For ease of understanding, the following discussion is subdivided into three areas of emphasis. The first section discusses certain intracranial electrodes; the second section relates to select embodiments of neurostimulation systems; and the third section outlines methods in accordance with other embodiments of the invention.

B. Intracranial Electrodes

FIGS. 2-15 illustrate intracranial electrodes in accordance with various embodiments of the invention. Like reference numbers are used throughout these figures to designate like or analogous elements.

Figure 2A:
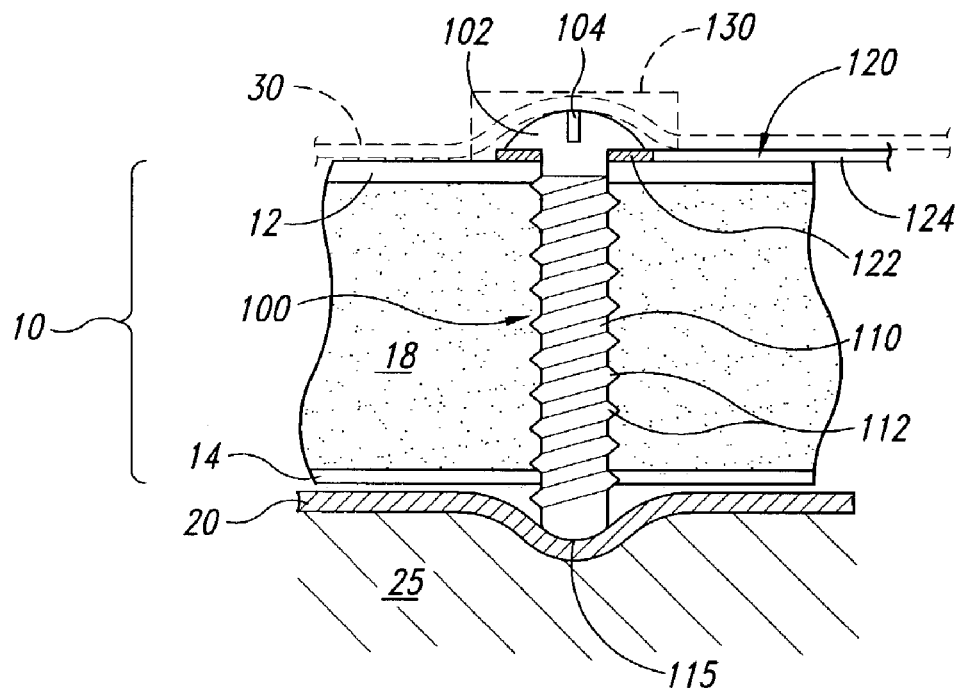
FIG. 2A is a schematic view in partial cross section of an intracranial electrode in accordance with one embodiment of the invention implanted in a patient.
Figure 2B:
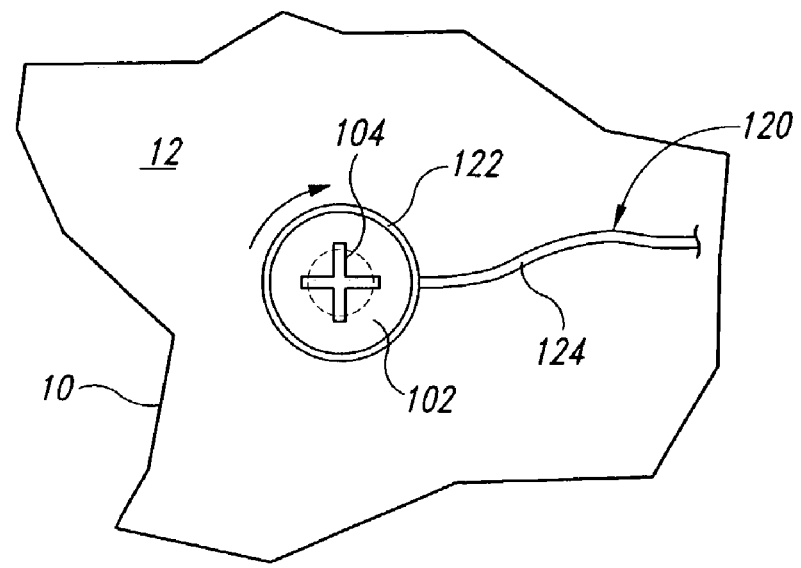
FIG. 2B is a schematic top elevation view of the implanted intracranial electrode of FIG. 2A.

FIGS. 2A-B illustrate an intracranial electrode 100 in accordance with one embodiment of the invention. This electrode 100 includes a head 102 attached to a threaded shaft 110. The head 102 and shaft 110 may be integrally formed of an electrically conductive material, e.g., titanium or another biocompatible, electrical conductive metal. The head 102 may include one or more slots 104, an alien head recess (not shown), or other structure (e.g., a square drive or TORX™ drive recess) adapted to facilitate turning the electrode 100. As the electrode 100 is turned, the threads 112 of the threaded shaft 110 will advance a generally distally positioned contact surface 115 of the electrode 100 toward the dura mater 20. The length of the shaft 110 may be selected so that the contact surface 115 of the electrode 100 electrically engages the surface of the dura mater 20 without causing undue harm to the dura mater 20 or the underlying cerebral cortex. The contact surface 115 may comprise a relatively blunt end to reduce trauma to the dura mater and the underlying brain tissue 25.

In one embodiment, the intracranial electrode 100 is adapted to be electrically connected to a pulse system (1050 in FIG. 18, for example), as described below. The electrode 100 may be connected to the pulse system in any desired fashion. In the illustrated embodiment, the electrode 100 is coupled to such a pulse system by means of an electrical lead 120. The electrical lead 120 shown in FIGS. 2A and 2B comprises an elongated, subcutaneously implantable body 124, which may have an insulative sheath. An electrically conductive ring or washer 122 may be attached to an end of the body 124. In one embodiment, an opposite end of the body 124 is physically attached to a component of the pulse system. In other embodiments, the leads may be operatively connected to one or more components of the pulse system without being physically attached thereto, e.g., using a transmitter and antenna or a magnetic coupling. Embodiments of pulse systems incorporating such wireless links are disclosed in U.S. Patent Application Publication No. U.S. 2002/0087201, the entirety of which is incorporated herein by reference.

The head 102 of the electrode 100 is adapted to be implanted subcutaneously beneath the patient's scalp 30 (shown schematically in FIG. 2A). As explained below, the electrode 100 may be used to deliver an electrical signal to the brain tissue 25 adjacent the contact surface 115. At higher stimulus levels, electrical contact between the patient's scalp 30 and the head 102 of the electrode 100 may be uncomfortable for the patient. If so desired, the scalp 30 may be electrically insulated from the head 102. This may be accomplished by applying on the head 102 a quantity of a dielectric, biocompatible, cementitious material (not shown), which may be cured or dried in place. In another embodiment, the head 102 may be covered with a separate cap 130 (shown in dashed lines in FIG. 2A) formed of a dielectric material, e.g., a dielectric, biocompatible plastic, that may be glued, press-fit, or otherwise attached to the head 102 and/or the lead 120.

The dimensions of the electrode 100 can be varied to meet various design objectives. In one embodiment, however, the electrode 100 is longer than the thickness of the patient's skull. More specifically, the head 102 is adapted to be seated at an extracranial subcutaneous site while the threaded shaft 110 is only slightly longer than the skull thickness at the intended treatment site. Lengths on the order of 4-50 mm, for example, may be appropriate in certain applications. The diameter of the head 102 and the threaded shaft 110 may also be varied. For most applications, shafts 110 having diameters (typically excluding the width of the threads 112) of no greater than 4 mm will suffice. Shaft diameters of about 14 mm are likely, with diameters of 1.5-2.5 mm being well suited for most applications. FIGS. 2A-B illustrate an electrode 100 having a constant diameter shaft 110, but it should be understood that the shaft diameter may vary. For example, the shaft 110 may taper distally to improve the ability of the shaft 110 to be self-tapping. The head 102 typically will have a larger diameter than an adjoining portion of the shaft 110. (It should be recognized that FIGS. 2-15 are not drawn to scale. In particular, the aspect ratio of the electrodes is significantly reduced to better illustrate certain functional aspects of the designs.)

Figure 3A:
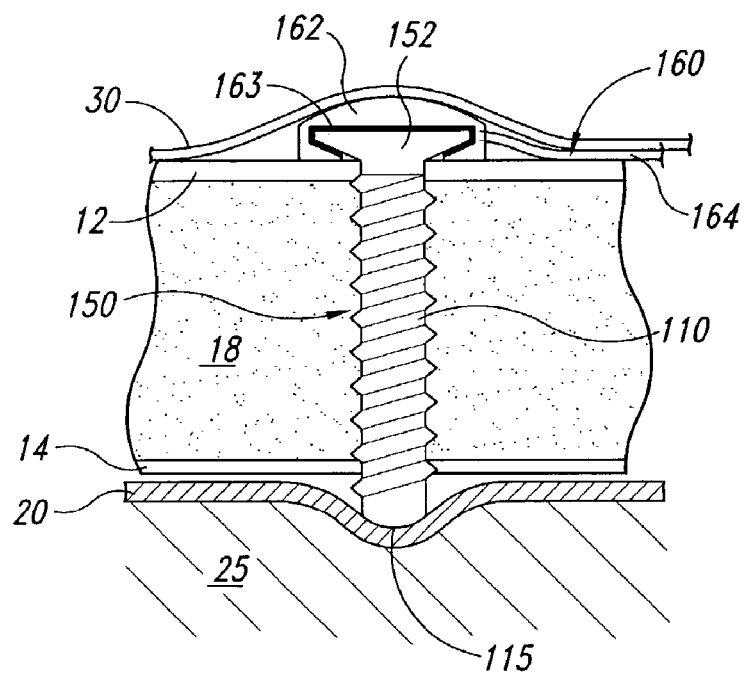
FIG. 3A is a schematic illustration in partial cross section of an intracranial electrode in accordance with another embodiment of the invention implanted in a patient.

FIG. 3A illustrates an intracranial electrode 150 in accordance with another embodiment of the invention. This intracranial electrode 150 is similar in many respects to the intracranial electrode 100 of FIGS. 2A-B. For example, the electrode 150 includes an electrically conductive threaded shaft 110 defining a blunt, atraumatic contact surface 115 adjacent a distal end.

Figure 3B:
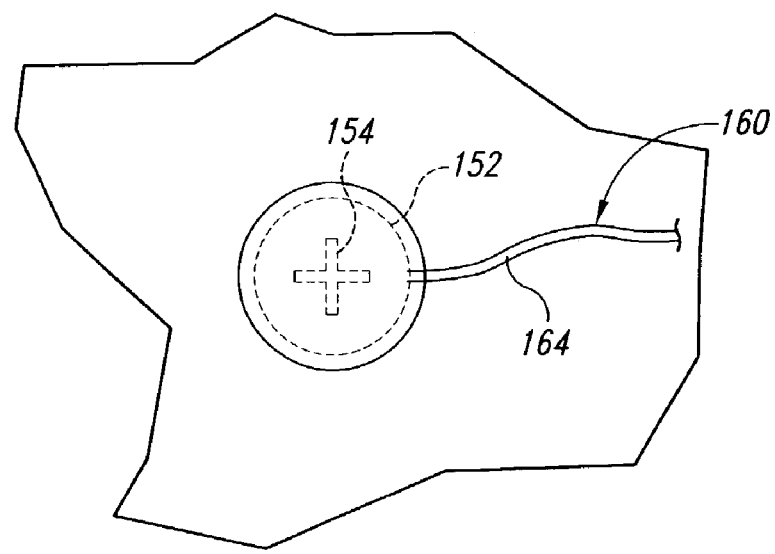
FIG. 3B is a schematic top elevation view of the implanted intracranial electrode of FIG. 3A.

The connection of the electrode 150 to the lead 160 in FIGS. 3A-B differs somewhat from the connection of the electrode 100 and lead 120 in FIGS. 2A-B, however. In FIGS. 2A-B, the electrode 100 is electrically coupled to the lead 120 by compressively engaging the electrically conductive ring 122 of the lead 120 between the electrode head 102 and the skull 10. In FIGS. 3A-B, the electrode 150 includes a head 152 including slots 154 or other structure for engaging a screwdriver, wrench, or the like. The head 152 is adapted to engage a cap 162 carried by the lead 160 that electrically couples the body 164 of the lead 160 to the head 152 of the electrode 150. In the illustrated embodiment, the cap 162 comprises a dielectric body (e.g., a dielectric plastic material with some resilience) having an electrically conductive inner surface 163, which may be provided by coating an interior surface of the cap 162 with a metal. In one embodiment, the cap 162 is adapted to resiliently deform to be press-fitted on the head 152. The body 164 of the lead 160 may be coupled to the electrically conductive inner surface 163 of the cap 162, thereby providing an electrical pathway between the electrode 150 and a pulse system (not shown) operatively coupled to the lead 160.

In one embodiment, the cap 162 is sized to be subcutaneously implanted beneath the patient's scalp 30. In the illustrated embodiment, the head 152 and the cap 162 both extend outwardly beyond the outer cortex 12 of the patient's skull 10. In another embodiment (not shown) some or all of the length of the head 152 and/or the cap 162 may be countersunk into a recess formed through the outer cortex 12 and/or an outer portion of the cancellous 18. This can improve patient comfort, which can be useful if the intracranial electrode 150 is intended to be implanted permanently or for an extended period of time.

FIGS. 4A-B schematically illustrate aspects of an intracranial electrode 200 in accordance with another embodiment. The electrode 200 may comprise an electrically conductive inner portion 205 and an electrically insulative outer portion 206. In the illustrated embodiment, the electrically conductive portion 205 of the electrode 200 includes a head 202 and a threaded shaft 210 defining a contact surface 215 for electrically contacting the patient's dura mater 20. These elements of the electrode 200 and their electrical connection to the lead 120 are directly analogous to the electrode 100 shown in FIGS. 2A-B. The electrically insulative outer portion 206 of the electrode 200 shown in FIG. 4A comprises a dielectric member 240 that is disposed between the threaded shaft 210 and the patient's skull 10. As shown in FIG. 4B, this dielectric member 240 may take the form of a tapered sleeve. The sleeve 240 may have an upper ring-like portion 242 and a plurality of deformable flanges 244 extending distally therefrom. The flanges 244 may be adapted to be urged outwardly into compressive contact with a bore formed in the patient's skull 10 when the threaded shaft 210 is advanced into the interior of the sleeve 240. Although not shown in FIG. 4B, ribs or teeth may be provided on the exterior surfaces of the flanges 244 to further anchor the sleeve 240 in the cancellous 18. In one embodiment, the sleeve 240 is formed of a dielectric plastic and the threads of the threaded member 210 may be self-tapping in the inner wall of the sleeve 240.

When implanted in a skull 10 as shown in FIG. 4A, the dielectric sleeve 240 will electrically insulate the skull 10 from the electrically conductive shaft 210 of the electrode 200. (The sleeve 240 need not completely electrically isolate the skull and shaft 210; it merely serves to reduce electrical conduction to the skull 10.) As explained below, some embodiments of the invention employ an array comprising a plurality of intracranial electrodes implanted at various locations in a patient's skull 10. The use of a dielectric member such as the dielectric sleeve 240 can help electrically isolate each of the electrodes 200 from other electrodes 200 in the array (not shown). If so desired, the electrode 200 may be provided with a dielectric cap 230 sized and shaped to be implanted subcutaneously beneath the patient's scalp 30 (not shown in FIG. 4A). Much like the cap 130 of FIG. 2A, this cap 230 may electrically insulate the patient's scalp from the electrically conductive head 202. This may further improve electrical isolation of the electrodes 200 in an array.

FIG. 5 illustrates an intracranial electrode 250 in accordance with yet another embodiment of the invention. This electrode 250 includes an electrically conductive shaft 260 electrically coupled to a subcutaneously implantable head 262 and a distally positioned contact surface 265. The shaft 260 is received in the interior of an externally threaded dielectric layer 280. The shaft 260 may be operatively coupled to the dielectric layer 280 for rotation therewith as the electrode is threadedly advanced through the patient's skull 10. In one embodiment, this may be accomplished by a spline connection between the shaft 260 and the dielectric layer 280. In other embodiments, the dielectric layer 280 may be molded or otherwise formed about the shaft 260.

In one particular embodiment, the dielectric layer 280 comprises an electrically insulative ceramic material. In another embodiment, the dielectric layer 280 comprises an electrically insulative plastic or other biocompatible polymer that has sufficient structural integrity to adequately anchor the electrode 250 to the skull 10 for the duration of its intended use. If so desired, the dielectric layer 280 may be porous or textured to promote osseointegration of long-term implants. For shorter-term applications, the dielectric layer 280 may be formed of or covered with a material that will limit osseointegration.

In each of the preceding embodiments, the intracranial electrode 100, 150, 200, or 250 has a fixed length. In the embodiment shown in FIGS. 2A-B, for example, the distance between the base of the head 102 and the contact surface 115 remains fixed. When the threaded shaft 110 is sunk into the skull 10 to a depth sufficient to compress the conductive ring 122 of the lead 120 between the head 102 and the skull 10, this will also fix the distance from the exterior surface of the outer cortex 12 of the skull 10 to the contact surface 115. The thickness of the skull 10 can vary from patient to patient and from site to site on a given patient's skull. Hence, the pressure exerted by the contact surface 115 against the dura mater 20 will vary depending on the thickness of the skull. If the electrode 100 is selected to be long enough to make adequate electrical contact with the dura mater adjacent the thickest site on a skull, the pressure exerted by the contact surface 115 against the dura mater 20 may cause undue damage at sites where the skull is thinner. Consequently, it can be advantageous to provide a selection of electrode sizes from which the physician can choose in selecting an electrode 100 for a particular site of a specific patient's skull.

FIGS. 6-12 illustrate embodiments of electrodes with adjustable lengths.

Figure 6A:
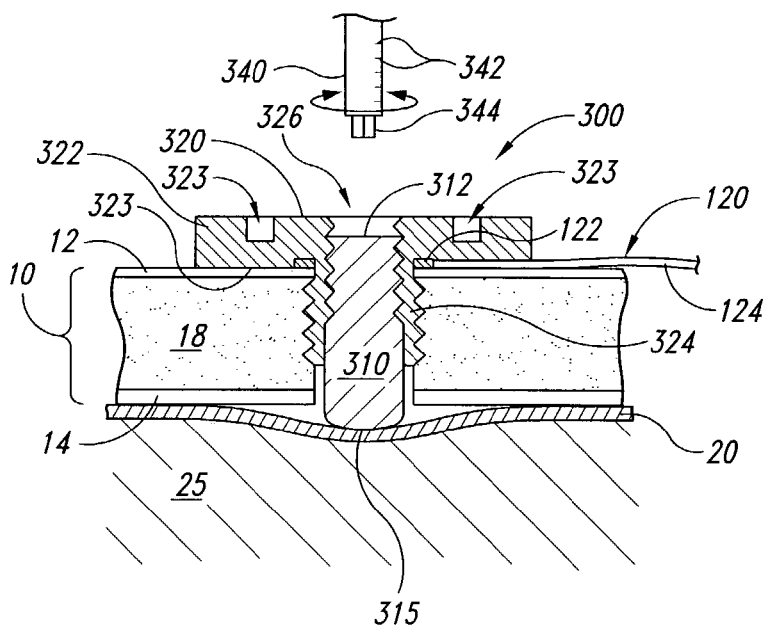
FIG. 6A is a schematic illustration in partial cross section of an intracranial electrode in accordance with a further embodiment of the invention implanted in a patient.
Figure 6B:
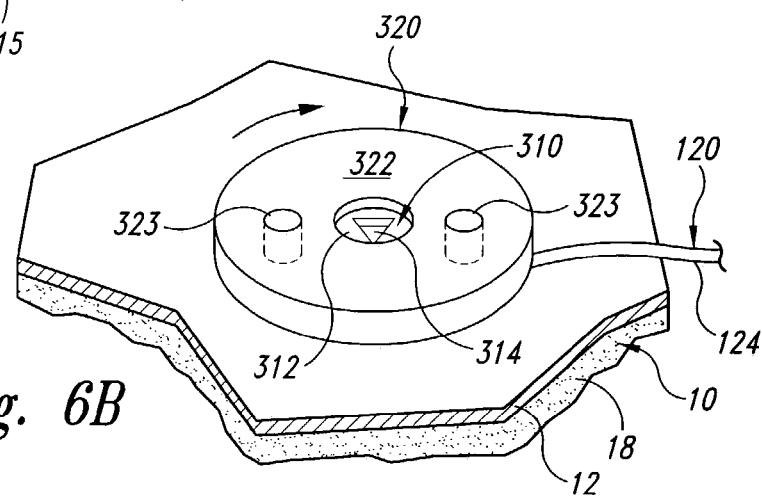
FIG. 6B is a schematic top elevation view of the implanted intracranial electrode of FIG. 6A.

FIGS. 6A-B, for example, illustrate an intracranial electrode 300 that is adapted to adjust a distance between the outer surface of the skull 10 and a contact surface 315 of the electrode 300. This, in turn, enables the contact force between the contact surface 315 and the surface of the dura mater 20 to be varied without requiring multiple electrode lengths.

The intracranial electrode 300 of FIGS. 6A and 6B includes a probe or shaft 310 that has a blunt distal surface defining the contact surface 315 of the electrode 300. The shaft 310 has a proximal end 312 that may include a torque drive recess 314 or the like to facilitate rotation of the shaft 310 relative to a head 320 of the electrode 300. At least a portion of the length of the shaft 310 is externally threaded. In the illustrated embodiment, the shaft has an externally threaded proximal length and an unthreaded surface along a distal length.

The head 320 of the electrode 300 comprises a body 322 and a tubular length 324 that extends from the body 322. The body 322 may be adapted to be rotated by hand or by an installation tool. In one embodiment the body 322 is generally hexagonal to facilitate rotation with an appropriately sized wrench. In the particular embodiment shown in FIGS. 6A-B, the body 322 has a pair of recesses 323 in its outer face sized and shaped to interface with a dedicated installation tool (not shown) having projections adapted to fit in the recesses 323. If so desired, the installation tool may be a torque wrench or other tool adapted to limit the amount of torque an operator may apply to the head 320 of the electrode 300 during installation. The tubular length 324 may be externally threaded so the head 320 may be anchored to the skull 10 by screwing the tubular length 324 into the skull 10.

The head 320 includes an internally threaded bore 326 that extends through the thickness of the body 322 and the tubular length 324. The bore 326 has threads sized to mate with the external threads on the shaft 310. If so desired, a biocompatible sealant (e.g., a length of polytetrafluoroethylene tape) may be provided between the threads of the bore 326 and the threads of the shaft 310 to limit passage of fluids or infectious agents through the bore 326.

Rotation of the shaft 310 with respect to the head 320 will, therefore, selectively advance or retract the shaft 310 with respect to the head 320. This will, in turn, increase or decrease, respectively, the distance between the lower face 323 of the head body 322 and the contact surface 315 of the shaft 310. As suggested in FIG. 6A, this may be accomplished by inserting a tip 344 of a torque driver 340 into the torque drive recess 314 in the shaft 310 and rotating the torque driver 340. The tip 344 of the torque driver 340 may be specifically designed to fit the torque drive recess 314. In the embodiment shown in FIGS. 6A-B, the torque drive recess 314 is generally triangular in shape and is adapted to receive a triangular tip 344 of the torque driver 340. If so desired, the torque driver 340 may comprise a torque wrench or the like that will limit the maximum torque and operator can apply to the shaft 310 of the electrode 300.

If so desired, the torque driver 340 may include graduations 342 to inform the physician how far the shaft 310 has been advanced with respect to the head 320. As noted below, in certain methods of the invention, the thickness of the skull at the particular treatment site may be gauged before the electrode 300 is implanted. Using this information and the graduations 342 on the torque driver 340, the physician can fairly reliably select an appropriate length for the electrode 300 to meet the conditions present at that particular site.

In the embodiment shown in FIGS. 6A-B, the head 320 and the shaft 310 are both formed of an electrically conductive material. The conductive ring 122 of the lead 120 may be received in a slot formed in the lower face 323 of the body 322. Alternatively, the ring 122 may be internally threaded, permitting it to be threaded over the external threads of the tubular length 324 before the head 320 is implanted. If so desired, the ring 122 can instead be compressively engaged by the lower face 323 of the head 320 in a manner analogous to the engagement of the head 102 with the ring 122 in FIG. 2A, for example.

In another embodiment, the head 320 is formed of a dielectric material, such as a dielectric ceramic or plastic. This may necessitate a different connection between the lead 120 and the shaft 310, such as by electrically contacting the lead 120 to the proximal end 312 of the shaft 310. Employing a dielectric head 320 can help electrically insulate the skull 10 from the electrodes 300, improving signal quality and reducing interference between the various electrodes 300 in an array, as noted above.

Figure 7:
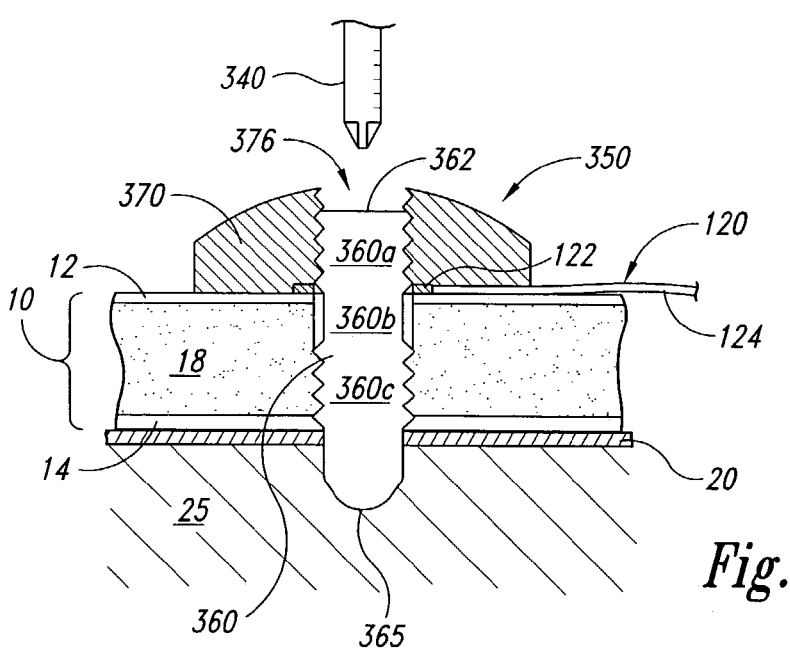
FIG. 7 is a schematic illustration in partial cross section of an intracranial electrode in accordance with still another embodiment of the invention implanted in a patient.
Figure 8:
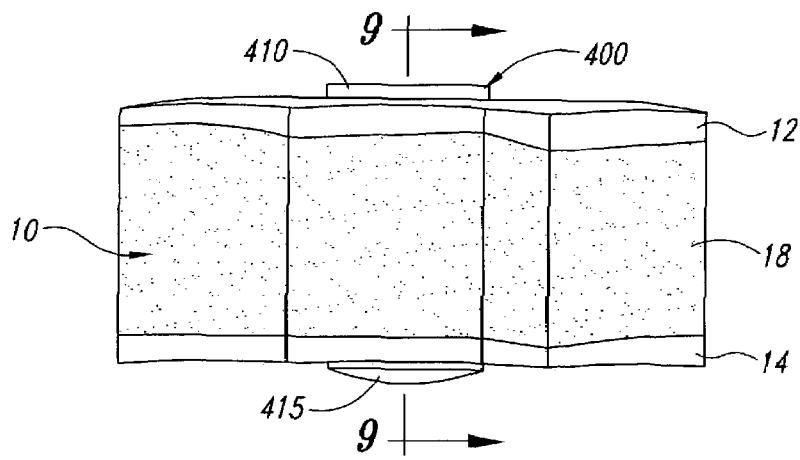
FIG. 8 is a schematic side view of a broken-away portion of a patient's skull in which an intracranial electrode in accordance with another embodiment of the invention has been implanted.
Figure 9:
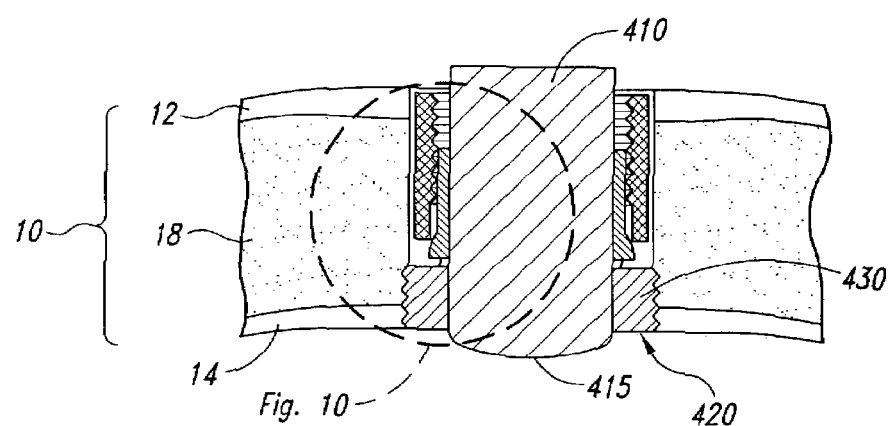
FIG. 9 is a schematic partial cross-sectional view taken along line 9-9 of FIG. 8.
Figure 10:
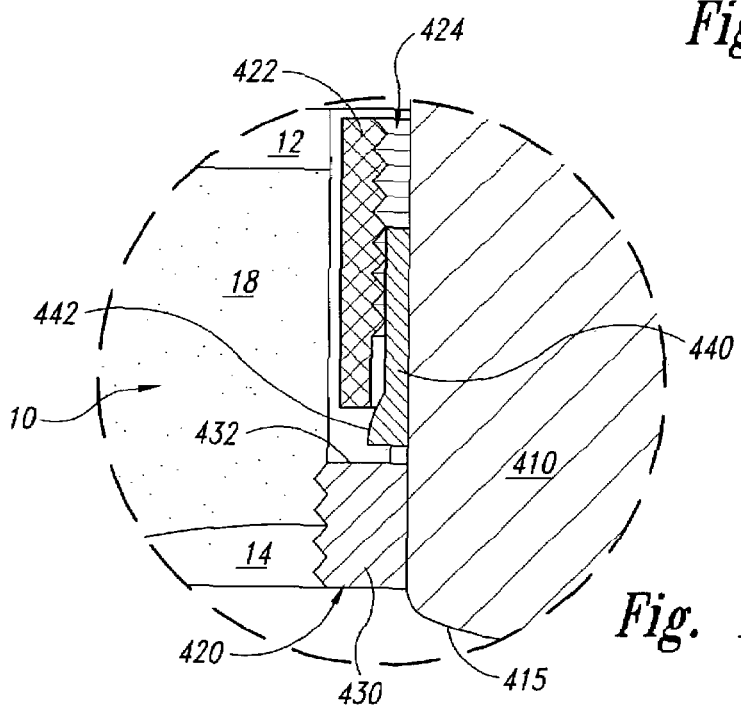
FIG. 10 is an isolation view of a portion of the implanted electrode of FIG. 9.
Figure 11:
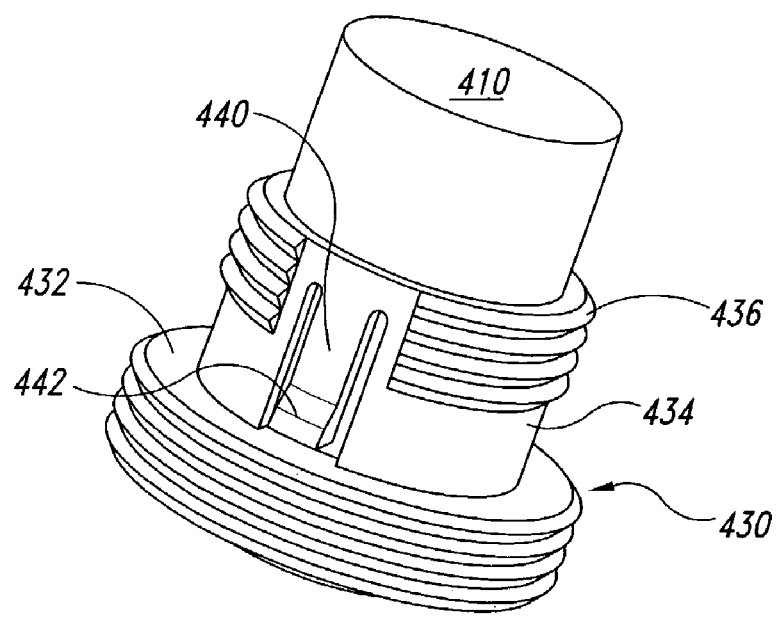
FIG. 11 is a perspective view of selected components of the intracranial electrode of FIGS. 8-10.

FIG. 7 schematically illustrates an intracranial electrode 350 in accordance with a further embodiment of the invention. The electrode 350 includes a shaft or probe 360 having a proximal end 362 and a distally located contact surface 365. The shaft 360 may include a first threaded portion 360a and a second threaded portion 360c. In the embodiment shown in FIG. 7, the first and second threaded portions 360a and 360c are separated by an unthreaded intermediate portion 360b. In an alternative embodiment, the two threaded portions 360a and 360c directly abut one another.

The intracranial electrode 350 of this embodiment also includes a head 370 having an internally threaded bore 376 extending through its thickness. The threads of the bore 376 are adapted to mate with the threads of the first threaded portion 360a. By rotating the shaft 360 with respect to the head 370 (e.g., with a screwdriver 340), the distance between the head 370 and the contact surface 365 can be adjusted in much the same manner described above in connection with FIGS. 6A-B.

The head 320 of the electrode 300 in FIGS. 6A-B has an externally threaded tubular length 324 that extends into the skull 10 and helps anchor the electrode 300 to the skull 10. The shaft 310 may then move with respect to the skull by rotating the shaft 310 with respect to the head 320. In the embodiment shown in FIG. 7, the head 370 is not directly anchored to the skull 10. Instead, the threads of the second threaded portion 360c are adapted to threadedly engage the skull 10 to anchor the electrode 350 with respect to the skull 10 and the head 370 is attached to the first threaded portion 360a of the shaft 360. In one embodiment, the shaft 360 may be threaded into a pilot hole in the skull 10. Once the shaft 360 is positioned at the desired depth, the head 370 may be screwed onto the first threaded portion 360a of the shaft 360 to help fix the shaft 360 with respect to the skull and provide a less traumatic surface to engage the patient's scalp (not shown) when the scalp is closed over the electrode 350. In another embodiment, the length of the electrode 350 may first be adjusted by rotating the shaft 360 with respect to the head 370. Once the electrode 350 has the desired length, the shaft 360 may be advanced into the skull 10. The shaft 360 may be graduated to facilitate adjustment to the appropriate length. If so desired, the first threaded portion 360a may be threaded in a direction opposite the second threaded portion 360c and/or the pitch of the threads in the first threaded portion 360a may be different from the pitch of the threads in the second threaded portion 360c.

In the embodiment of FIG. 7, the shaft 360 of the electrode 350 extends through the dura mater 20 and the contact surface 365 of the electrode 350 is in direct contact with the cerebral cortex of the patient's brain. This is simply intended to illustrate one alternative application. In other embodiments, the length of the electrode 350 may be selected so that the contact surface 365 electrically contacts the dura mater 20 without extending therethrough, much as illustrated in FIG. 6A, for example.

FIGS. 8-11 illustrate an intracranial electrode 400 in accordance with another embodiment of the invention. The intracranial electrode 400 includes a shaft or probe 410 that is slidably received by a head 420. The shaft 410 comprises an electrically conductive material and defines an electrical contact surface 415, e.g., on its distal end.

In the preceding embodiments, some or a majority of the head of the electrode extends outwardly beyond the outer surface of the skull 10. In the particular implementation shown in FIGS. 8-10, the head 420 is received entirely within the thickness of the skull 10. It should be understood, though, that this is not necessary for operation of the device, and this is shown simply to highlight that the position of the head 420 with respect to the skull 10 can be varied. In another embodiment, at least a portion of the head 420 extends outwardly beyond the outer surface of the skull 10.

The head 420 includes a base 430 and an actuator 422. The base 430 includes an externally threaded body 432 and a tubular length 434 that extends from the body 432. A portion of the tubular length 434 carries external threads 436. The tubular length 434 may also include one or more locking tabs 440, each of which includes an actuating surface 442.

The actuator 422 has an internally threaded bore 424 that is adapted to matingly engage the threads 436 on the base 430. Rotating the actuator 422 with respect to the base 430 in a first direction will advance the actuator 422 toward the actuating surface 442 of each of the tabs 440. The actuator 422 may urge against the actuating surfaces 442, pushing the tabs 440 inwardly into engagement with the shaft 410. This will help lock the shaft 410 in place with respect to the base 430. Rotating the actuator 422 in the opposite direction will allow the tabs 440 to resiliently return toward a rest position wherein they do not brake movement of the shaft 410. The force with which the shaft 410 engages the dura mater 20 (not shown) then can be adjusted to a desired level by moving the shaft 410 with respect to the base 430. When the shaft 410 is in the desired position, the actuator 422 may be moved into engagement with the tabs 440 to hold the shaft 410 in the desired position.

Figure 12:
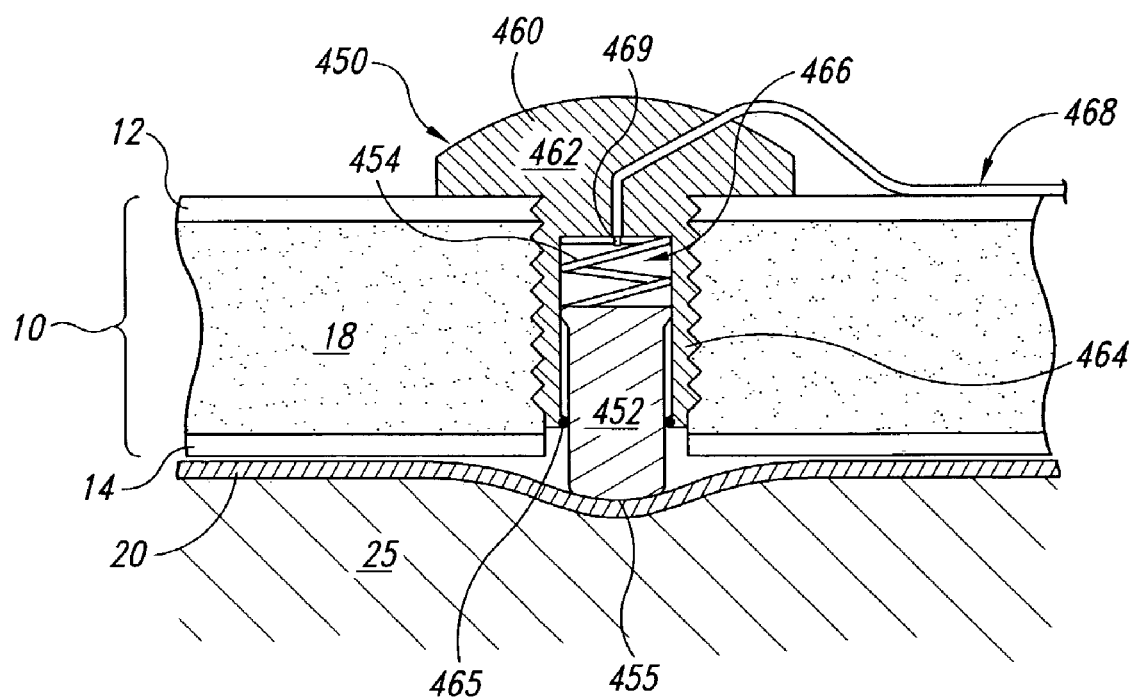
FIG. 12 is a schematic illustration in partial cross section of an intracranial electrode in accordance with yet another embodiment of the invention implanted in a patient.

FIG. 12 illustrates an adjustable-length intracranial electrode 450 in accordance with another embodiment. The intracranial electrode 450 includes an axially slidable probe or shaft 452 and a head 460. The head 460 includes a body 462 and an externally threaded tubular length 464. The tubular length 464 includes an axially extending recess 466 sized to slidably receive a portion of the shaft 452. An O-ring 465 or the like may provide a sliding seal between the head 460 and the shaft 452.

The contact surface 455 of the shaft 452 is pushed against the surface of the dura mater 20 with a predictable force by means of a spring 454 received in the recess 466. In FIG. 12, the spring 454 is typified as a compressed coil spring formed of a helically wound wire or the like. In this embodiment, an electrical contact 469 of the lead 468 may be electrically coupled to the wire of the spring 454. Electrical potential may then be conducted to the shaft 452 by the wire of the spring 454.

In another embodiment (not shown), the spring 454 comprises a compressed elastomer, which may take the form of a column that fills some or all of the diameter of the recess 466. The elastomer may comprise a biocompatible polymeric material, for example. In such an embodiment, the elastomer may be electrically conductive, e.g., by filling a polymeric material with a suitable quantity of a conductive metal powder or the like. In another embodiment, one or more wires may be embedded in the elastomeric material to conduct an electrical signal across the elastomer to the shaft 452.

In the illustrated embodiment and the alternative embodiment wherein the spring 454 comprises an elastomer, the head 460 may be formed of a dielectric material, helping electrically insulate the skull 10 from the shaft 452. In an alternative embodiment, the head 460 may be formed of an electrically conductive material. Even though the other structural elements of the electrode 450 may remain largely the same, this would avoid the necessity of having the lead 468 extend through the head 460; an electrically conducive ring 122 or the like instead may be employed in a manner analogous to that shown in FIG. 6A, for example.

Figure 13:
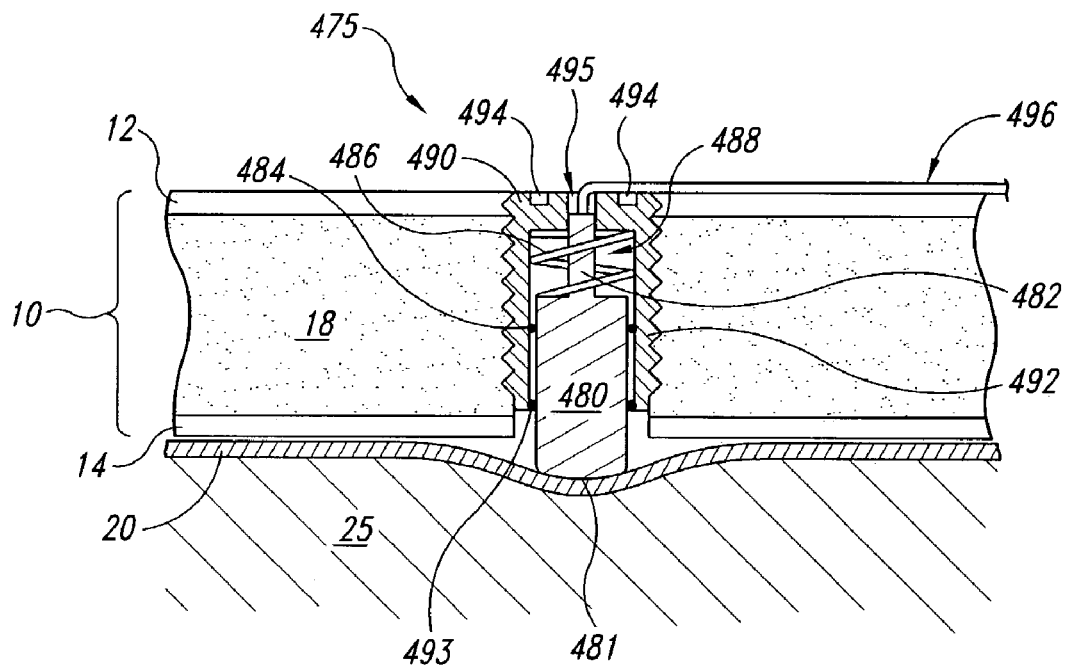
FIG. 13 is a schematic illustration in partial cross section of an intracranial electrode in accordance with one more embodiment of the invention implanted in a patient.

FIG. 13 depicts and adjustable-length intracranial electrode 475 in accordance with a different embodiment. Some aspects of the intracranial electrode 475 are similar to the intracranial electrode 450 shown in FIG. 12. In particular, the intracranial electrode 475 includes an axially slidable probe or shaft 480 that is slidably received in an axially extending recess 488 in a tubular length 492 of a head 490. A proximal face of the body 490 may include a pair of tool-receiving recesses 494, which may be analogous to the tool-receiving recesses 323 noted above in connection with FIG. 6A, to aid in the installation of the body 490. If so desired, one or more seals may be provided between the shaft 480 and the body 490. In the embodiment shown in FIG. 13, the body 490 carries a first O-ring 493 and the shaft 480 and carries a second O-ring 484 sealed against the interior of the recess 488. These O-rings may also serve as abutments to limit axial travel of the shaft 480 in the recess 488.

The contact surface 481 of the shaft 480 is pushed against the surface of the dura mater 20 with a predictable force by means of a spring 486. The spring 486 may be substantially the same as the spring 454 shown in FIG. 12, and the various materials suggested above for the spring 454 may also be employed in the spring 486 of FIG. 13.

In FIG. 12, the spring 454 provides the electrical connection between the lead 468 and the shaft 452. In the embodiment of FIG. 13, however, the lead 496 may be connected directly to the shaft 480 through a lumen 495 in the body 490. This lumen 495 is sized to slidably receive a reduced-diameter neck 482 of the shaft 480. As the body 490 is screwed into the skull 10 and moves toward the brain 25, contact between the shaft 480 and the dura mater 20 will urge the shaft 480 upwardly, moving the neck 482 upwardly within the lumen 495.

The electrode 475 of FIG. 13 may facilitate delivering a highly reproducible contact force of the contact surface 481 of the shaft 480 against the dura mater 20. The position of the reduced-diameter neck 482 of the shaft 480 within the lumen 495 will vary in a fixed relationship with the force exerted on the spring 486 by the shaft 480. Since the force of the shaft 480 against the spring 486 is essentially the same as the force of the shaft 480 against the dura mater 20, knowing the position of the neck 482 within the lumen 495 can give the operator an indication of the force exerted against the dura mater 20. In one particular embodiment, the interior of the lumen 495 may be graduated to mark off the depth of the neck 482 in the lumen 495. In another embodiment, the body 490 may be driven into the skull 10 until the height of the neck 482 in the lumen 495 reaches a predetermined point, e.g., when the top of the neck 482 is flush with the top of the body 490.

Figure 14:
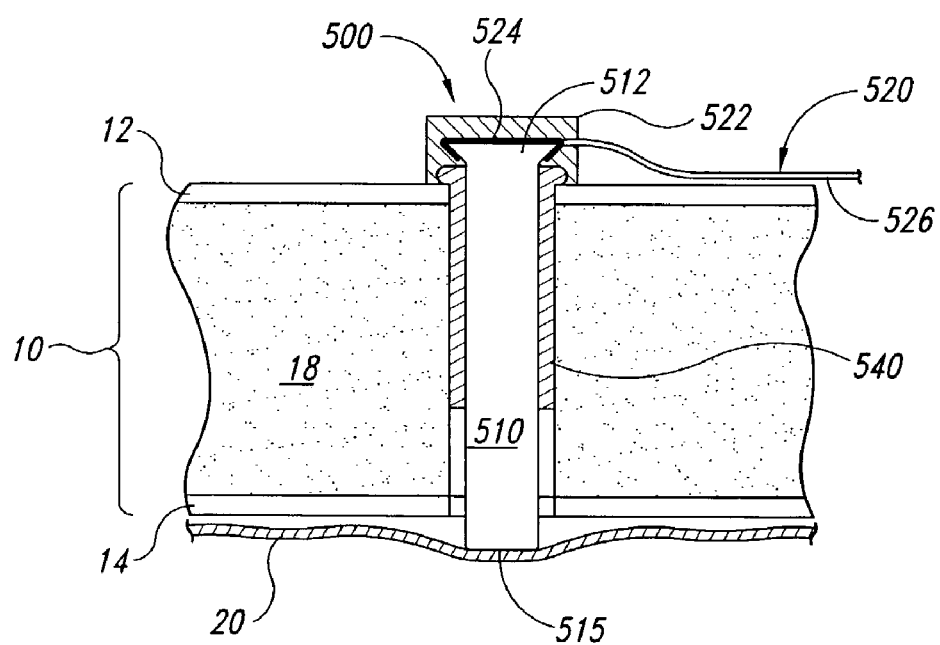
FIG. 14 is a schematic illustration in partial cross section of an intracranial electrode in accordance with a further embodiment of the invention implanted in a patient.
Figure 15:
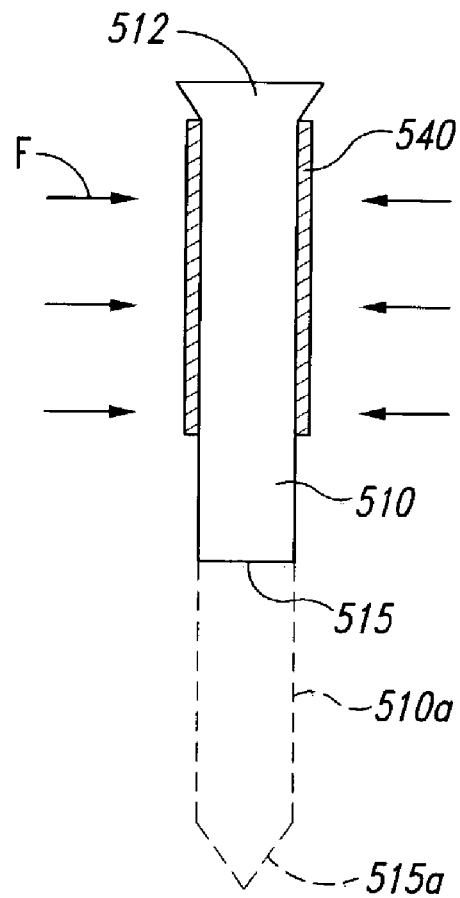
FIG. 15 is a schematic partial cross-sectional view of the intracranial electrode of FIG. 13 with a retaining collar of the electrode in a radially compressed state.
Figure 16:
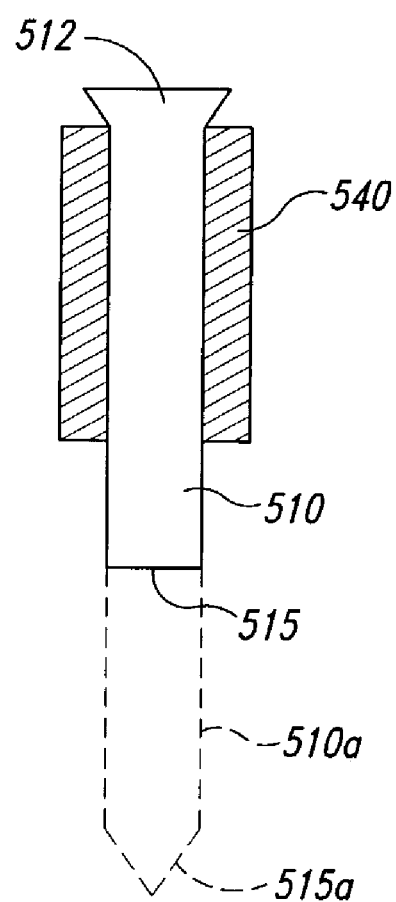
FIG. 16 is a schematic partial cross-sectional view of the intracranial electrode of FIG. 14 with the retaining collar in a radially expanded state.

FIG. 14 illustrates an intracranial electrode 500 in accordance with still another embodiment of the invention. This electrode 500 includes an electrically conductive probe or shaft 510 having a head 512 and a contact surface 515. A radially compressible retaining collar 540 extends along a portion of the length of the shaft 510. As shown in FIG. 15, the retaining collar 540 may be adapted to assume a radially reduced configuration in response to a compressive force, indicated schematically by the arrows F. This compressive force F may be generated by collapsing the retaining collar 540 and restraining it in the lumen of an introducing sheath (not shown) sized to be received in a bore through the skull 10. When this force F is removed (e.g., by retracting the introducing sheath), the retaining collar 540 may expand radially outwardly away from the shaft 510, as illustrated in FIG. 16.

To implant the electrode 500 in the skull 10, the shaft 510 may be advanced into a bore in the skull until the contact surface 515 exerts the desired contact force against the dura mater 20. Once the shaft 510 is in the desired position, the compressive force F on the collar 540 may be released, allowing the collar 540 to expand outwardly into compressive engagement with the lumen of the bore in the skull 10. This will help hold the electrode 500 in place with respect to the skull without requiring permanent anchoring of the shaft 510 to the skull 10.

The shaft 510 may be electrically coupled to a pulse system (not shown) by a lead 520. The lead 520 may include a cap 522 having an electrically conductive inner surface 524 coupled to a body 526 of the lead. The lead 520 may be analogous to the lead 160 shown in FIGS. 3A-B. Any other suitable electrical connection between the shaft 510 and the pulse system may be employed.

In one embodiment, the collar 540 comprises a dielectric material. This will help electrically insulate the skull 10 from the shaft 510. In another embodiment, the collar 540 is electrically conductive and the lead 520 may be electrically coupled to the shaft 510 via the collar 540.

In the embodiment shown in FIG. 14, the shaft 510 may have a length only a little longer than the thickness of the patient's skull 10 and the contact surface 515 may be relatively blunt. Such a design is useful for relatively atraumatic contact with the dura mater 20. In another embodiment suggested in dashed lines in FIGS. 15 and 16, the electrode 500 may instead have a substantially longer shaft 510*a* and a relatively sharp contact surface 515*a*. Such an embodiment may be useful for directly stimulating a particular location within the cerebral cortex or some other location within the deeper tissues of the brain.

Figure 17:
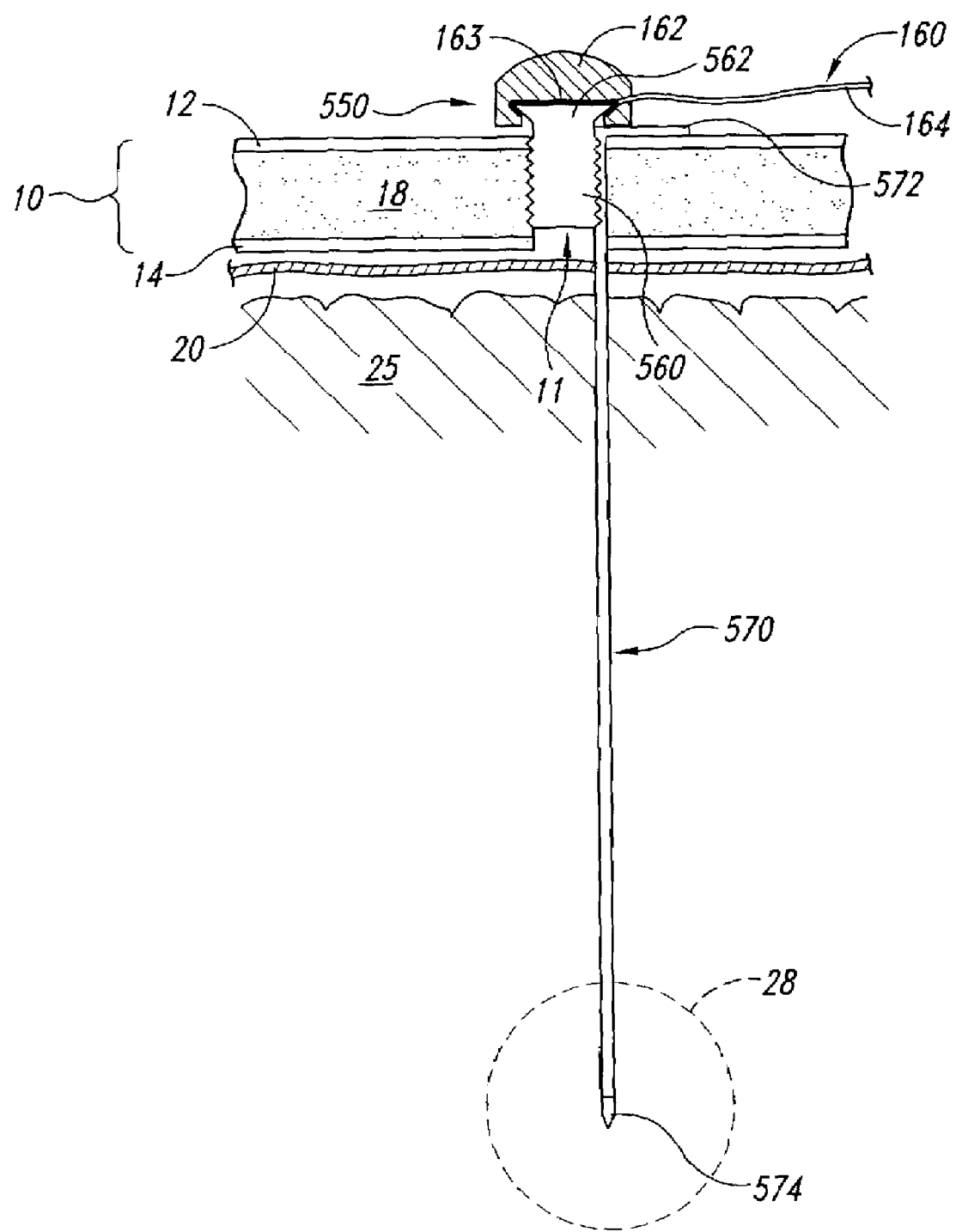
FIG. 17 is a schematic illustration in partial cross section of a deep brain intracranial electrode in accordance with an alternative embodiment of the invention implanted in a patient.

FIG. 17 schematically illustrates how certain principles of the invention can be embodied in a deep brain intracranial electrode 550. The electrode 550 generally includes a threaded shaft 560 having a head 562. The head 562 may be coupled to a pulse system or a sensing unit (as described below) via a lead 160 in the same manner lead 160 is attached to the head 152 of electrode 150 in FIGS. 3A-B. (Like reference numbers are used in these figures to indicate like elements.) The electrode 550 also includes an elongate conductive member 570 that extends inwardly from the skull 10 to a selected target site 28. The conductive member 570, which may comprise a length of a conductive wire, may be electrically shielded by a dielectric sheath along much of its length and have an exposed, electrically conductive tip 574.

In use, the conductive member 570 may be slid freely through a pilot hole 11 formed through the skull to position the tip 574 at the target site 28 in a known manner. The pilot hole 11 may be larger than the conductive member 570 or be tapped to receive the threads of the shaft 560. With the conductive member 570 in place, the shaft 560 may be threaded into the pilot hole 11, crimping the conductive member 570 against an interior of the pilot hole 11. This will fix the conductive member 570 in place. If so desired, a proximal length 572 of the conductive member 570 may extend outwardly of the skull and be held in place by the head 562. The threads of the threaded shaft 560 may also cut through the dielectric sheath of the conductive member 570 as the shaft 560 is screwed into place, making electrical contact with the conductive wire therein.

Figure 18:
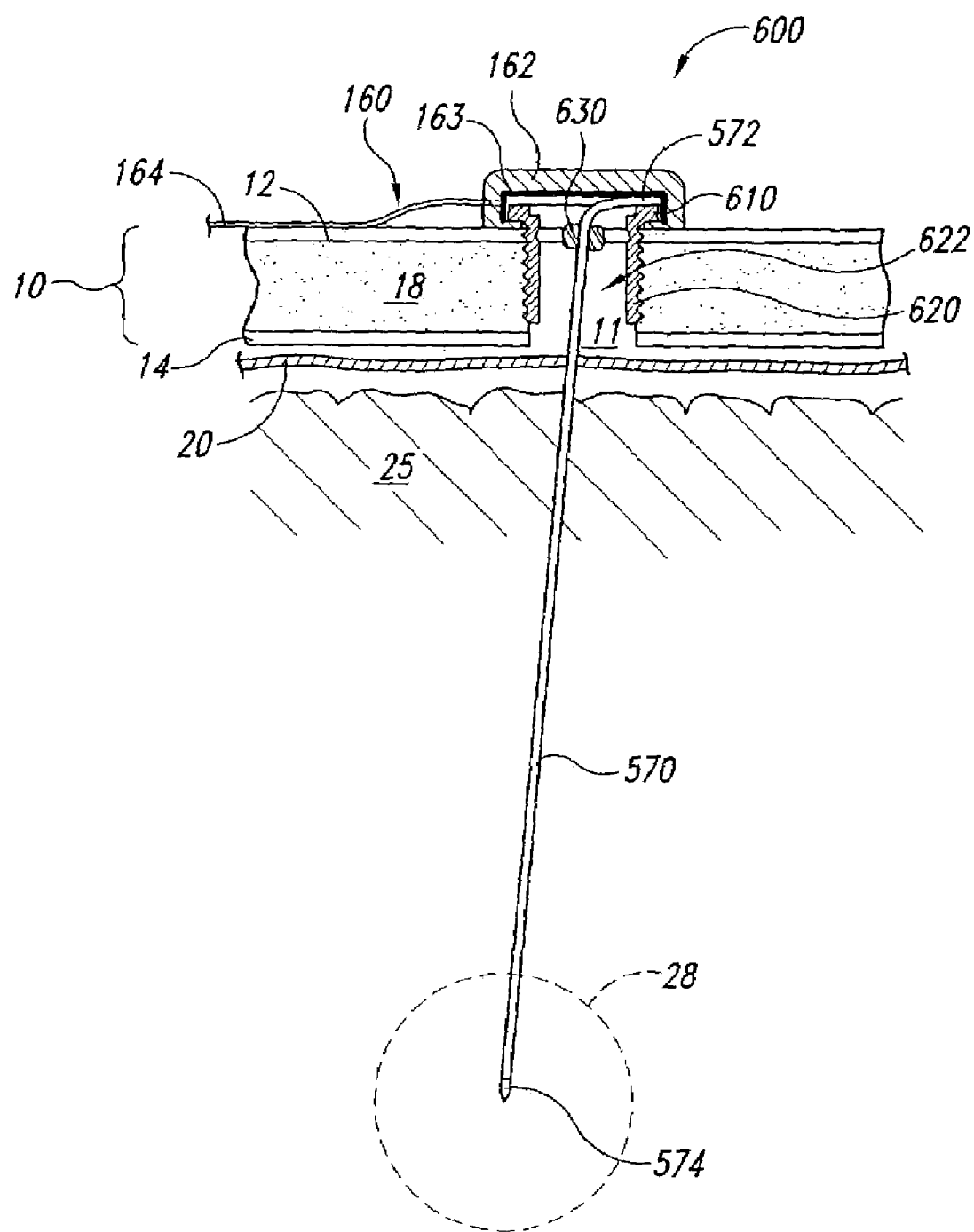
FIG. 18 is a schematic illustration in partial cross section of a deep brain intracranial electrode in accordance with still another embodiment of the invention implanted in a patient.

FIG. 18 schematically illustrates a deep brain intracranial electrode 600 in accordance with an alternative embodiment of the invention. This electrode 600 includes a head 610 having a threaded shaft 620 with an axially-extending opening 622 extending through the length of the head 610. The head 610 may also include a gimbal fitting 630 adapted to slidably receive a length of a conductive member, which may comprise the same type of elongate conductive member 570 discussed above in connection with FIG. 17.

The gimbal fitting 630 is adapted to allow an operator greater control over the placement of the electrically conductive tip 574 of the conductive member 570. In use, the tip 574 of the conductive member 570 will be threaded through an opening in the gimbal fitting 630. By pivoting the gimbal fitting 630 with respect to the threaded shaft 620 of the head 610, the angular orientation of the conductive member 570 with respect to the pilot hole 11 in the skull 10 can be accurately controlled. Once the operator determines that the conductive member 570 is at the appropriate angle, e.g., using a surgical navigation system such as that noted below, the operator may advance the conductive member 570 to position the conductive tip 574 at the target site 28. Once the tip 574 is in position, the cap 162 of a lead 160 may be press-fitted on the head 610 of the electrode 600. This will crimp the proximal length 572 of the conductive member 570 between the head 610 and the conductive inner surface 163 of the cap 162, providing an effective electrical connection between the conductive member 570 and the body 164 of the lead 160.

C. Systems Employing Intracranial Electrodes

Figure 19:
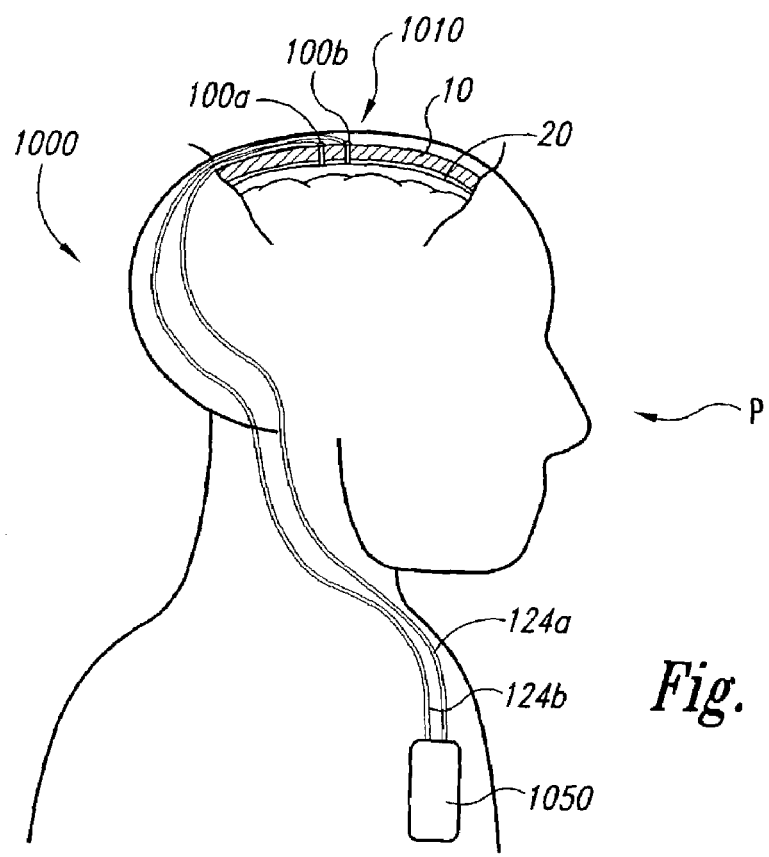
FIG. 19 is a schematic overview of a neurostimulation system in accordance with a further embodiment of the invention.

FIG. 19 is a schematic illustration of a neurostimulation system 1000 in accordance with one embodiment of the invention. This neurostimulation system 1000 includes an array 1010 of intracranial electrodes and an internally implantable pulse system 1050. The array 1010 of electrodes may employ one or more electrodes in accordance with any one or more of the embodiments described above in connection with FIGS. 2-18 or any other suitable design. In the particular implementation depicted in FIG. 19, the array 1010 (shown schematically in FIG. 20) includes a first implantable intracranial electrode 100*a* and a second implantable intracranial electrode 100*b*, each of which may be substantially the same as the electrode 100 shown in FIGS. 2A-B. These electrodes 100*b* and 100*b* extend through the skull 10 into contact with the dura mater 20 at two spaced-apart locations.

The pulse system 1050 may be implanted in the body of the patient P at a location remote from the array 1010 of electrodes 100. In the embodiment shown in FIG. 19, the pulse system 1050 is adapted to be implanted subclavicularly. In the alternative embodiment shown in FIG. 20, the pulse system 1050 is adapted to be implanted in a recess formed in the patient's skull 10. In either embodiment, each of the electrodes 100 in the array 1010 is electrically coupled to the pulse system 1050 by means of a separate lead (120 in FIGS. 2A-B) having an elongate, subcutaneously implantable body 124. Hence, electrode 100a is coupled to the pulse system 1050 by the elongate body 124a of a first lead and the other electrode 100b is coupled to the pulse system 1050 by the elongate body 124b of another lead. In one embodiment, the elongate bodies 124a-b are combined into a single subcutaneously implantable cable or ribbon.

Figure 21:
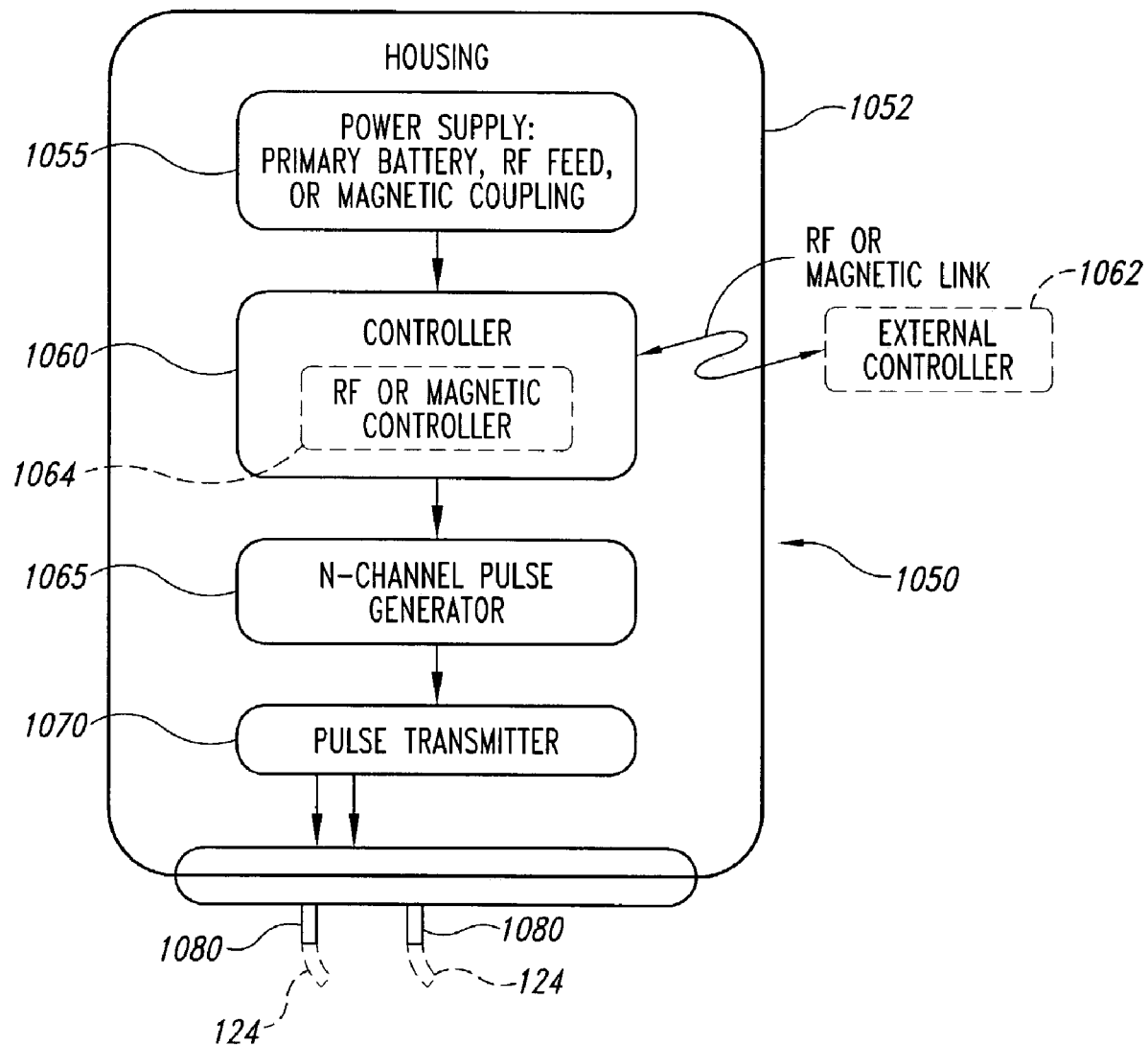
FIG. 21 is a schematic illustration of one pulse system suitable for use in the neurostimulation system of FIG. 17 or FIG. 18.
Figure 22:
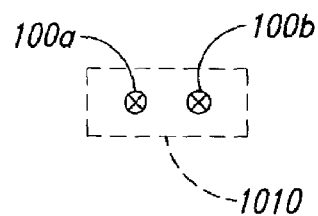
FIG. 22 is a schematic top view of the array of electrodes in FIG. 17.

FIG. 21 schematically illustrates one pulse system 1050 suitable for use in the neurostimulation system 1000 shown in FIG. 19. The pulse system 1050 generally includes a power supply 1055, an integrated controller 1060, a pulse generator 1065, and a pulse transmitter 1070. The power supply 1055 can be a primary battery, such as a rechargeable battery or other suitable device for storing electrical energy. In alternative embodiments, the power supply 1055 can be an RF transducer or a magnetic transducer that receives broadcast energy emitted from an external power source and converts the broadcast energy into power for the electrical components of the pulse system 1050.

In one embodiment, the controller 1060 includes a processor, a memory, and a programmable computer medium. The controller 1060, for example, can be a computer, and the programmable computer medium can be software loaded into the memory of the computer and/or hardware that performs the requisite control functions. In an alternative embodiment suggested by dashed lines in FIG. 21, the controller 1060 may include an integrated RF or magnetic controller 1064 that communicates with an external controller 1062 via an RF or magnetic link. In such a circumstance, many of the functions of the controller 1060 may be resident in the external controller 1062 and the integrated portion 1064 of the controller 1060 may comprise a wireless communication system.

The controller 1060 is operatively coupled to and provides control signals to the pulse generator 1065, which may include a plurality of channels that send appropriate electrical pulses to the pulse transmitter 1070. The pulse generator 1065 may have N channels, with at least one channel associated with each of N electrodes 100 in the array 1010. The pulse generator 1065 sends appropriate electrical pulses to the pulse transmitter 1070, which is coupled to a plurality of electrodes 1080. In one embodiment, each of these electrodes is adapted to be physically connected to the body 124 of a separate lead, allowing each electrode 1080 to electrically communicate with a single electrode 100 in the array 1010 on a dedicated channel of the pulse generator 1065. Suitable components for the power supply 1055, the integrated controller 1060, the pulse generator 1065, and the pulse transmitter 1070 are known to persons skilled in the art of implantable medical devices.

Figure 20:
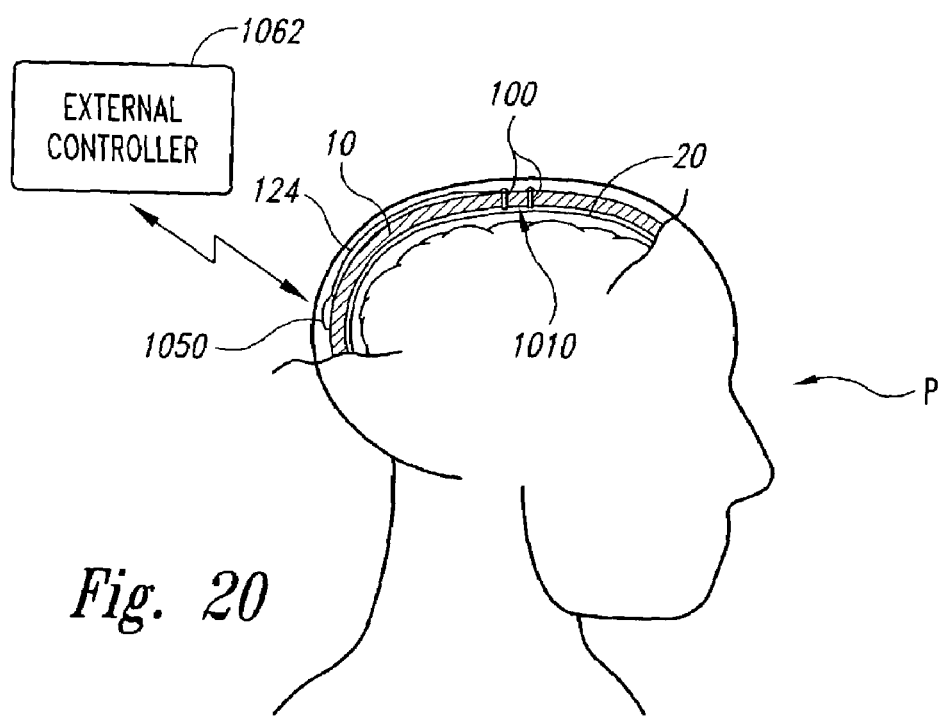
FIG. 20 is a schematic overview of a neurostimulation system in accordance with another embodiment of the invention.
Figure 23:
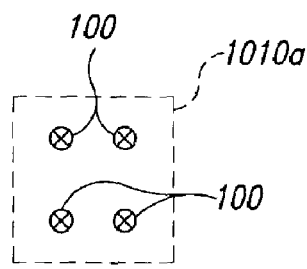
FIGS. 23-26 are schematic top views of alternative electrode arrays in accordance with other embodiments of the invention.
Figure 24:
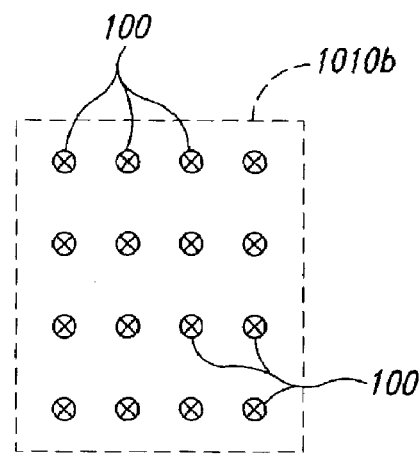
Figure 25:
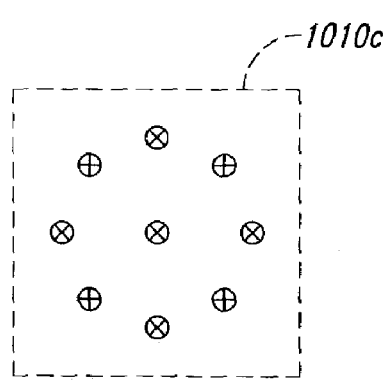
Figure 26:
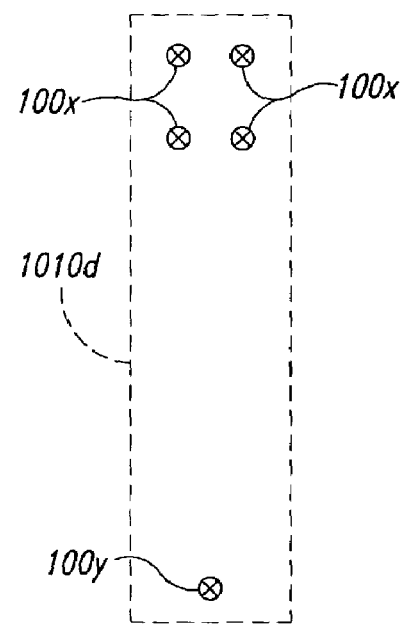

As shown in FIG. 20, the array 1010 of electrodes 100 in FIG. 19 comprises a simple pair of electrodes 100a and 100b implanted in the patient's skull at spaced-apart locations. FIGS. 23-26 illustrate alternative arrays that may be useful in other embodiments. In FIG. 23, the array 1010a includes four electrodes 100 arranged in a rectangular array. The array 1010b of FIG. 24 includes sixteen electrodes 100, also arranged in a rectangular array. The array 1010c shown in FIG. 25 includes nine electrodes 100 arranged in a radial array. FIG. 26 illustrates an array 1010d that includes four electrodes 100x arranged in a rectangular pattern and a fifth electrode 100y at a location spaced from the other four electrodes 100x. In using such an array, the four proximate electrodes 100x may be provided with the same polarity and the fifth electrode 100y may have a different polarity. In some embodiments, the housing (1052 in FIG. 19) of the pulse system 1050 may serve the function of the fifth electrode 100y. The precise shape, size, and location of the array 1010 and the number of electrodes 100 in the array 110 can be optimized to meet the requirements of any particular application.

The electrodes 100 of these arrays 1010 may be provided with electrical signals in a variety of different manners. In some circumstances, one electrode 100 or a subset of the electrodes 100 may have one electrical potential and a different electrode 100 or subset of the electrodes 100 (or, in some embodiments, the housing 1052 of the pulse system 1050) may have a different electrical potential. U.S. patent application Ser. No. 09/978,134, entitled "Systems and Methods for Automatically Optimizing Stimulus Parameters and Electrode Configurations for Neuro-Stimulators" and filed Oct. 15, 2001 (the entirety of which is incorporated herein by reference), suggests ways for optimizing the control of the electrical pulses delivered to the electrodes 100 in an array 1010. The methods and apparatus disclosed therein may be used to automatically determine the configuration of therapy electrodes and/or the parameters for the stimulus to treat or otherwise effectuate a change in neural function of a patient.

The preceding discussion focuses on use of intracranial electrodes (e.g., electrodes 100, 150, 200, 250, 300, 350, 400, 450, 475, 500, 550, or 600) in neurostimulation systems. In an alternative application, the intracranial electrodes may be used to monitor electrical potentials in electroencephalography. A suitable electroencephalograph may incorporate a system similar to the neurostimulation system 1000 shown in FIG. 19, but a sensing unit (not shown) may be used in place of the pulse system 1050. Suitable components for such a sensing unit are known to those skilled in the art of electroencephalography.

D. Methods

As noted above, other embodiments of the invention provide methods of implanting an intracranial electrode and/or methods of installing a neurostimulation system including an implantable intracranial electrode. In the following discussion, reference is made to the particular intracranial electrode 100 illustrated in FIGS. 2A-B and to the neurostimulation system 1000 shown in FIG. 19. It should be understood, though, that reference to this particular embodiment is solely for purposes of illustration and that the methods outlined below are not limited to any particular apparatus shown in the drawings or discussed in detail above.

As noted above, implanting conventional cortical electrodes typically requires a full craniotomy under general anesthesia to remove a relatively large (e.g., thumbnail-sized or larger) window in the skull. Craniotomies are performed under a general anesthetic and subject the patient to increased chances of infection.

In accordance with one embodiment of the present invention, however, the diameter of the electrode shaft 110 is sufficiently small to permit implantation under local anesthetic without requiring a craniotomy. In this embodiment, a relatively small (e.g., 4 mm or smaller) pilot hole may be formed through at least part of the thickness of the patient's skull adjacent a selected stimulation or monitoring site of the brain. When implanting the electrode 100 of FIGS. 2A-B, it may be advantageous to extend the pilot hole through the entire thickness of the skull. Care should be taken to avoid undue trauma to the brain in forming the pilot hole. In one embodiment, an initial estimate of skull thickness can be made from MRI, CT, or other imaging information. A hand-held drill may be used to form a bore shallow enough to avoid extending through the entire skull. A stylus may be inserted into the pilot hole to confirm that it strikes relatively rigid bone. The drill may then be used to deepen the pilot hole in small increments, checking with the stylus after each increment to detect when the hole passes through the thickness of the inner cortex 14 of the skull 10. If so desired, the stylus may be graduated to allow a physician to measure the distance to the springy dura mater and this information can be used to select an electrode 100 of appropriate length or, if an adjustable-length electrode (e.g., electrode 300 of FIGS. 6A-B) is used, to adjust the electrode to an appropriate length.

The location of the pilot hole (and, ultimately the electrode 100 received therein) can be selected in a variety of fashions. U.S. Patent Application Publication No. U.S. 2002/0087201 and U.S. application Ser. No. 09/978,134 (both of which are incorporated hereinabove), for example, suggest approaches for selecting an appropriate stimulation site. When the desired site has been identified, the physician can bore the pilot hole to guide the contact surface 115 of the electrode 100 to that site. In one embodiment, the physician may use anatomical landmarks, e.g., cranial landmarks such as the bregma or the sagittal suture, to guide placement and orientation of the pilot hole. In another embodiment, a surgical navigation system may be employed to inform the physician during the procedure. Briefly, such systems may employ real-time imaging and/or proximity detection to guide a physician in placing the pilot hole and in placing the electrode 100 in the pilot hole. In some systems, fiducials are positioned on the patient's scalp or skull prior to imaging and those fiducials are used as reference points in subsequent implantation. In other systems, real-time MRI or the like may be employed instead of or in conjunction with such fiducials. A number of suitable navigation systems are commercially available, such as the STEALTHSTATION TREON TGS sold by Medtronic Surgical Navigation Technologies of Louisville, Colo., U.S.

Once the pilot hole is formed, the threaded electrode 100 may be advanced along the pilot hole until the contact surface 115 electrically contacts a desired portion of the patient's brain. If the electrode 100 is intended to be positioned epidurally, this may comprise relatively atraumatically contacting the dura mater 20; if the electrode is to contact a site on the cerebral cortex, the electrode will be advanced to extend through the dura mater. The electrodes 100 may also be implanted to a selected depth within the cerebral cortex or at a deeper location in the brain.

In one embodiment, the length of the electrode 100 is selected (or adjusted for electrode 300, for example) to achieve the desired level of contact and the electrode will be advanced until a known relationship with the skull is achieved, e.g., when the head 102 compresses the contact ring 122 of the lead 120 against the exterior of the skull 10. In another embodiment, the thickness of the skull 10 need not be known to any significant accuracy before the electrode 100 is implanted. Instead, the electrode 100 may be connected, e.g., via the lead 120, to an impedance monitor and the impedance may be monitored as the electrode 100 is being implanted. It is anticipated that the measured impedance will change when the electrode 100 contacts the dura mater 20. Once this contact is detected, the physician may advance the electrode a small, fixed distance to ensure reliable electrical contact over time.

As noted above, the electrode 100 may be coupled to a lead 120. The timing of this coupling may vary with the nature of the coupling. For a lead 120 employing a contact ring 122 or the like positioned below the head 102, the lead may be coupled to the electrode before the electrode is introduced into the skull. In other embodiments, the lead (e.g., lead 160 of FIGS. 3A-B) may be coupled to the electrode after the electrode is properly positioned with respect to the selected site of the brain. The lead, or at least a length thereof, may be implanted subcutaneously, e.g., by guiding it through a tunnel formed between the implant site and the intended site of a subclavicularly implanted pulse system 1050. The patient's scalp may then be closed over the head 102 of the electrode 100 so the electrode is completely enclosed. This can materially improve patient comfort compared to more convention systems wherein epilepsy monitoring electrodes or the like extend through the scalp to an extracorporeal connection.

Once the electrode is in place, an electrical stimulus may be delivered from a pulse system 1050 to the patient's brain via the lead 120 and the electrode 100. In certain embodiments of the invention discussed previously, a plurality of electrodes 100 may be implanted in an array (e.g., array 1010, 1010a, 1010b, or 1010c) in the patient's skull and each of the electrodes 100 may be coupled to the pulse system 1050 by an electrically separate lead 120. The precise nature of the stimulus delivered via the electrode(s) 100 can be varied as desired to diagnose or treat any particular condition. The type and frequency of stimulus may be selected as outlined in U.S. patent application Publication No. U.S. 2002/0087201, for example, and also may be optimized as taught in U.S. application Ser. No. 09/978,134.

Unless the context clearly requires otherwise, throughout the description and the claims, the words "comprise," "comprising," and the like are to be construed in an inclusive sense as opposed to an exclusive or exhaustive sense, that is to say, in a sense of "including, but not limited to." Words using the singular or plural number also include the plural or singular number, respectively. When the claims use the word "or" in reference to a list of two or more items, that word covers all of the following interpretations of the word: any of the items in the list, all of the items in the list, and any combination of the items in the list.

The above-detailed descriptions of embodiments of the invention are not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, whereas steps are presented in a given order, alternative embodiments may perform steps in a different order. The various embodiments described herein can be combined to provide further embodiments.

In general, the terms used in the following claims should not be construed to limit the invention to the specific embodiments disclosed in the specification, unless the above-detailed description explicitly defines such terms. While certain aspects of the invention are presented below in certain claim forms, the inventors contemplate the various aspects of the invention in any number of claim forms.

Accordingly, the inventors reserve the right to add additional claims after filing the application to pursue such additional claim forms for other aspects of the invention.

What is claimed is:

1. A method for implanting an intracranial electrode, comprising:
    passing an elongate conductive member into a borehole extending through a patient's skull;
    advancing the elongate conductive member into the patient's brain so that the elongate conductive member extends into the patient's subcortical tissue; and
    threadably rotating a shaft of the electrode into engagement with a wall of the borehole to secure the shaft in the borehole and crimp the elongate conductive member against the wall of the borehole after advancing the elongate conductive member into the patient's brain.

2. The method of claim 1 wherein the elongate conductive member includes a dielectric coating, and wherein threadably rotating the shaft includes cutting through the dielectric coating with threads of the shaft to electrically couple the shaft to the elongate conductive member.

3. The method of claim 1, further comprising moving the elongate conductive member relative to the shaft before advancing the elongate conductive member into the patient's brain.

4. The method of claim 1, further comprising positioning a head associated with the shaft subcutaneously adjacent the patient's skull.

5. The method of claim 1, further comprising electrically coupling a lead to the shaft, and electrically coupling the shaft to the elongate conductive member.

6. The method of claim 1, further comprising electrically coupling the elongate conductive member to a pulse system.

7. The method of claim 1, further comprising engaging a cap with a head of the electrode to electrically couple a lead to the head.

8. The method of claim 7 wherein the cap includes a conductive inner surface, and wherein engaging the cap includes contacting the conductive inner surface with the head.

9. The method of claim 1, further comprising forming a pilot hole through at least a part of a thickness of the patient's skull adjacent a selected site of the patient's brain.

10. The method of claim 1, further comprising electrically coupling the elongate conductive member to a sensing unit.

11. An intracranial electrode system, comprising:
    a shaft;
    a head associated with the shaft, the head being sized to be positioned subcutaneously adjacent a patient's skull; and
    an elongate conductive member carried by at least one of the head and the shaft, the elongate conductive member being positioned to extend into the patient's subcortical tissue, the elongate conductive member and the shaft being movable relative to each other during implantation of the electrode in the patient, the elongate conductive member being electrically coupled to at least one of the shaft and the head, wherein at least one of the head and the shaft includes a rotatable fitting having an aperture, and wherein the elongate conductive member is slideably received in the aperture of the fitting, further wherein the rotatable fitting is rotatable relative to the shaft to change an orientation angle between an axial axis of the shaft and an axial axis of the elongate conductive member.

12. The system of claim 11, further comprising an anchor carried by at least one of the head and the shaft, the anchor being configured to fix the electrode with respect to the patient's skull.

13. The system of claim 12 wherein the anchor includes a plurality of threads carried by the shaft.

14. The system of claim 11, further comprising:
    a conductive lead electrically coupled to the head; and
    a subcutaneous cap positioned over the head and securing the lead to the head.

15. The system of claim 14 wherein the subcutaneous cap includes a conductive inner surface in electrical communication with both the lead and the head.

16. The system of claim 11, further comprising a pulse system electrically coupled to the elongate conductive member.

17. The system of claim 11, further comprising a sensing unit electrically coupled to the elongate conductive member.

18. The system of claim 11 wherein the intracranial electrode is one electrode in an array of intracranial electrodes.

19. An intracranial electrode system, comprising:
    a shaft;
    a head associated with the shaft, the head being sized to be positioned subcutaneously adjacent a patient's skull; and
    an elongate conductive member carried by at least one of the head and the shaft, the elongate conductive member being positioned to extend into the patient's subcortical tissue, the elongate conductive member and the shaft being movable relative to each other during implantation of the electrode in the patient, wherein at least one of the head and the shaft includes a rotatable fitting having an aperture, and wherein the elongate conductive member is slideably received in the aperture of the fitting, further wherein the rotatable fitting is rotatable relative to the shaft to change an orientation angle between an axial axis of the shaft and an axial axis of the elongate conductive member.

20. The system of claim 19 wherein the elongate conductive member is electrically coupled to one of the head and the shaft.

21. The system of claim 19, further comprising an anchor carried by at least one of the head and shaft, the anchor being configured to fix the electrode with respect to the patient's skull.

22. The system of claim 21 wherein the anchor includes a plurality of threads carried by the shaft.

23. The system of claim 19, further comprising:
    a conductive lead electrically coupled to the head; and
    a subcutaneous cap positioned over the head and securing the lead to the head.

24. The system of claim 23 wherein the subcutaneous cap includes a conductive inner surface in electrical communication with both the lead and the head.

25. The system of claim 19, further comprising a pulse system electrically coupled to the elongate conductive member.

26. The system of claim 19, further comprising a sensing unit electrically coupled to the elongate conductive member.

27. The system of claim 19 wherein the intracranial electrode is one electrode in an array of intracranial electrodes.

28. A method for implanting an intracranial electrode, comprising:
    securing a shaft of the electrode in a borehole extending through a patient's skull;

passing an elongate conductive member into the borehole;

while the shaft is in the borehole, rotating a fitting carried by the shaft relative to the shaft until an axis of an aperture through the fitting has a selected angular orientation relative to the shaft, then sliding the elongate member through the aperture in the fitting and into the patient's brain; and advancing the elongate conductive member into the patient's brain so that the elongate conductive member extends into the patient's subcortical tissue.

29. The method of claim 28, further comprising electrically coupling a lead to the shaft, and electrically coupling the shaft to the elongate conductive member.

30. The method of claim 28, further comprising positioning a head associated with the shaft subcutaneously adjacent the patient's skull.

31. The method of claim 28, further comprising engaging a cap with a head of the electrode to electrically couple a lead to the head.

32. The method of claim 31 wherein the cap includes a conductive inner surface, and wherein engaging the cap includes contacting the conductive inner surface with the head.

33. The method of claim 28, further comprising forming a pilot hole through at least a part of a thickness of the patient's skull adjacent a selected site of the patient's brain.

34. The method of claim 28, further comprising electrically coupling the elongate conductive member to a pulse system.

35. The method of claim 28, further comprising electrically coupling the elongate conductive member to a sensing unit.

36. The method of claim 28, further comprising determining the selected angular orientation and monitoring the axis of the aperture with a surgical navigation system.

* * * * *

UNITED STATES PATENT AND TRADEMARK OFFICE
CERTIFICATE OF CORRECTION

PATENT NO.       : 7,302,298 B2
APPLICATION NO.  : 10/418796
DATED            : November 27, 2007
INVENTOR(S)      : Lowry et al.

It is certified that error appears in the above-identified patent and that said Letters Patent is hereby corrected as shown below:

Front Page (56)
References Cited: Please insert the following references, previously cited in the IDS filed July 3, 2007, respectively, in compliance with 37 CFR 1.97:

--7,107,097      09/2006      Stern et al.

On title page (56) on page 4, under "Other Publications", in column 1, line 32, delete "afor" and insert -- for --, therefor.

On title page (56) on page 4, under "Other Publications", in column 1, line 60, delete "suppressess" and insert -- suppresses --, therefor.

On title page (56) on page 4, under "Other Publications", in column 2, line 14, delete "neurophysiology," and insert -- Neurophysiology, --, therefor.

On title page (56) on page 4, under "Other Publications", in column 2, line 38, delete "skilld" and insert -- skilled --, therefor.

On title page (56) on page 4, under "Other Publications", in column 2, line 54, delete "Domans" and insert -- Domains --, therefor.

On title page (56) on page 5, under "Other Publications", in column 1, line 25, delete "hemosphere" and insert -- hemisphere --, therefor.

On title page (56) on page 5, under "Other Publications", in column 2, line 40, delete "topogrpahy" and insert -- topography --, therefor.

On title page (56) on page 5, under "Other Publications", in column 2, line 67, delete "Treatement" and insert -- Treatment --, therefor.

On title page (56) on page 7, under "Other Publications", in column 1, line 2, delete "cells.""" and insert -- cells," --, therefor.

In column 1, line 8, delete "priority from" and insert -- benefit of U.S. --, therefor.

In column 1, line 63, after "TMS" delete ",".

In column 3, line 2, delete "patients'skulls." and insert -- patients' skulls. --, therefor.

UNITED STATES PATENT AND TRADEMARK OFFICE
CERTIFICATE OF CORRECTION

| | |
|---|---|
| PATENT NO. | : 7,302,298 B2 |
| APPLICATION NO. | : 10/418796 |
| DATED | : November 27, 2007 |
| INVENTOR(S) | : Lowry et al. |

It is certified that error appears in the above-identified patent and that said Letters Patent is hereby corrected as shown below:

In column 9, lines 3–9, delete "FIGS. 6A-B, for example, illustrate an intracranial electrode 300 that is adapted to adjust a distance between the outer surface of the skull 10 and a contact surface 315 of the electrode 300. This, in turn, enables the contact force between the contact surface 315 and the surface of the dura mater 20 to be varied without requiring multiple electrode lengths." and insert the same on Col. 9, Line 2, after "lengths." as the continuation of the paragraph.

Signed and Sealed this

Seventh Day of October, 2008

JON W. DUDAS
*Director of the United States Patent and Trademark Office*